(12) United States Patent
Del Poeta et al.

(10) Patent No.: US 10,463,722 B2
(45) Date of Patent: Nov. 5, 2019

(54) VACCINE COMPOSITIONS AGAINST PATHOGENIC FUNGI AND METHODS FOR USE THEREOF

(71) Applicant: THE RESEARCH FOUNDATION FOR THE STATE UNIVERSITY OF NEW YORK, Albany, NY (US)

(72) Inventors: Maurizio Del Poeta, Mount Sinai, NY (US); Antonella Rella, Port Jefferson Station, NY (US)

(73) Assignee: The Research Foundation for The State University of New York, Albany, NY (US)

(*) Notice: Subject to any disclaimer, the term of this patent is extended or adjusted under 35 U.S.C. 154(b) by 0 days.

(21) Appl. No.: 15/673,937

(22) Filed: Aug. 10, 2017

(65) Prior Publication Data

US 2018/0085442 A1 Mar. 29, 2018

Related U.S. Application Data

(60) Provisional application No. 62/372,894, filed on Aug. 10, 2016.

(51) Int. Cl.
| | |
|---|---|
| *C12N 9/26* | (2006.01) |
| *C12N 1/14* | (2006.01) |
| *A61K 39/00* | (2006.01) |
| *C12N 9/24* | (2006.01) |
| *C12P 19/44* | (2006.01) |
| *C12P 19/56* | (2006.01) |
| *C12P 33/00* | (2006.01) |
| *A61P 31/10* | (2006.01) |

(52) U.S. Cl.
CPC .......... *A61K 39/0002* (2013.01); *A61P 31/10* (2018.01); *C12N 9/2402* (2013.01); *C12P 19/44* (2013.01); *C12P 19/56* (2013.01); *C12P 33/00* (2013.01); *C12Y 302/01* (2013.01); *A61K 2039/52* (2013.01); *A61K 2039/522* (2013.01)

(58) Field of Classification Search
CPC .................................................. A61K 39/0002
USPC ......................................................... 435/201
See application file for complete search history.

(56) References Cited

PUBLICATIONS

Rella et al. Commentary: Role of Sterylglucosidase 1 (Sgl1) on the pathogenicity of Cryptococcus neoformans: potential applications for vaccine development, Oct. 9, 2015, pp. 1-3. (Year: 2015).*
Rella et al. Frontiers in Microbiology, Aug. 11, 2015, vol. 6, Article 836, pp. 1-11.*

* cited by examiner

*Primary Examiner* — Tekchand Saidha
(74) *Attorney, Agent, or Firm* — Scully, Scott, Murphy & Presser, P.C.

(57) ABSTRACT

The present disclosure provides compositions comprising mutant fungi include an inactive form of the sterylglucosidase enzyme. The present disclosure is also directed to vaccine based compositions, which include a mutant fungus that prohibit pathogenic fungal infection. This disclosure also provides methods for administering these compositions as a prophylaxis against fungal infection, as well as methods for isolating sterylglucosides that include the use of such mutant fungal compositions.

Figures 1A, 1B, 1C, 1D, 1E:
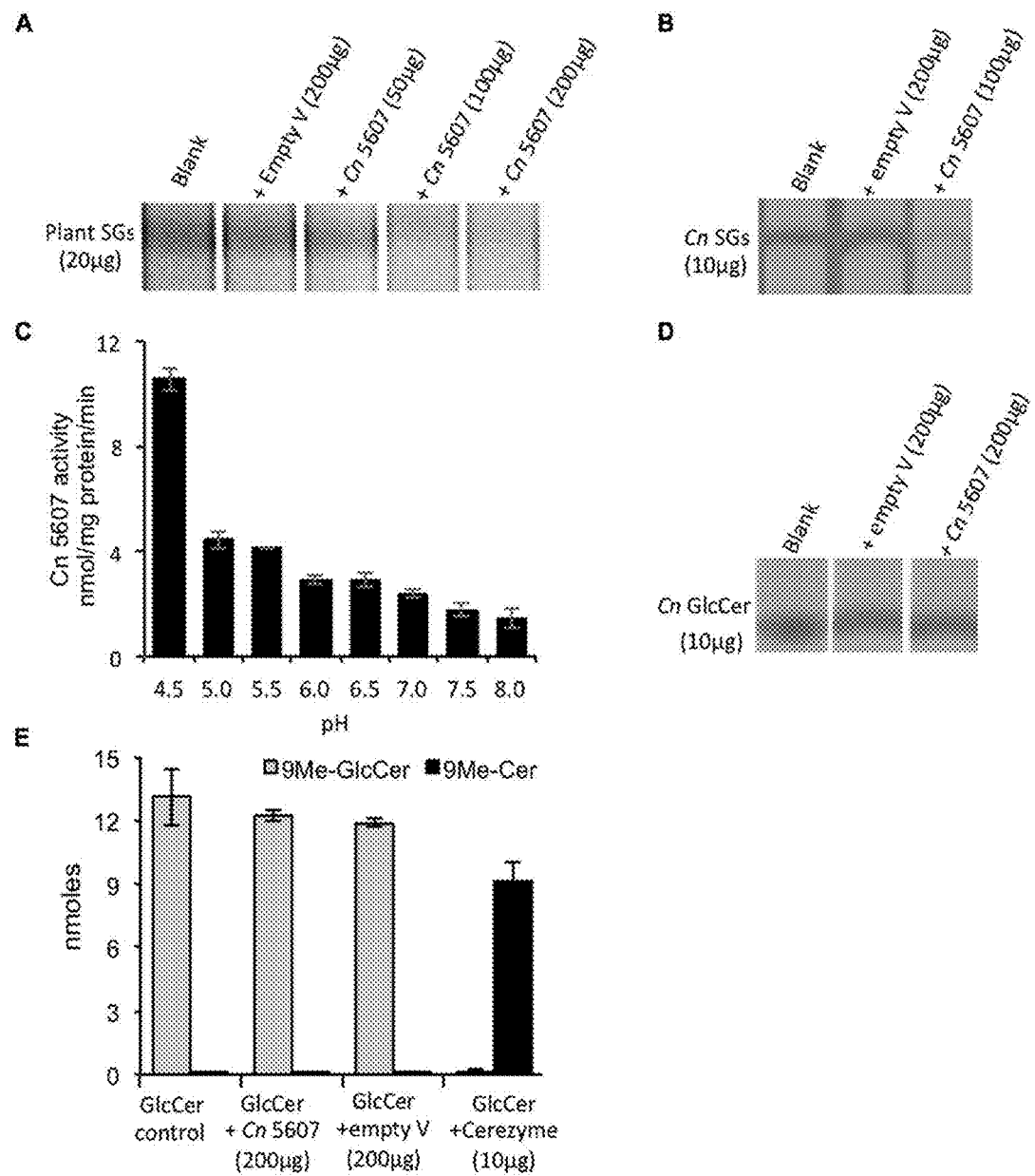

11 Claims, 18 Drawing Sheets
(9 of 18 Drawing Sheet(s) Filed in Color)
Specification includes a Sequence Listing.

Figure 5 (cont.)

```
SEQUENCE LISTING

<160> NUMBER OF SEQ ID NOS: 10

<210> SEQ ID NO 1
<211> LENGTH: 26
<212> TYPE: DNA
<213> ORGANISM: Artificial Sequence
<220> FEATURE:
<223> OTHER INFORMATION: oligonucleotide

<400> SEQUENCE: 1
gagctcatgc ctcctccacc agaagt                                        26

<210> SEQ ID NO 2
<211> LENGTH: 27
<212> TYPE: DNA
<213> ORGANISM: Artificial Sequence
<220> FEATURE:
<223> OTHER INFORMATION: oligonucleotide

<400> SEQUENCE: 2
tctagaagca ataacgcatt caggaca                                       27

<210> SEQ ID NO 3
<211> LENGTH: 36
<212> TYPE: DNA
<213> ORGANISM: Artificial Sequence
<220> FEATURE:
<223> OTHER INFORMATION: oligonucleotide

<400> SEQUENCE: 3
gtcaagctaa gagctccatt tgatcagcgg gattct                             36

<210> SEQ ID NO 4
<211> LENGTH: 36
<212> TYPE: DNA
<213> ORGANISM: Artificial Sequence
<220> FEATURE:
<223> OTHER INFORMATION: oligonucleotide
```

```
<400> SEQUENCE: 4
tccactccga actagtatcg cgtaaacgaa gaggtg                                36

<210> SEQ ID NO 5
<211> LENGTH: 36
<212> TYPE: DNA
<213> ORGANISM: Artificial Sequence
<220> FEATURE:
<223> OTHER INFORMATION: oligonucleotide

<400> SEQUENCE: 5
gtcaagctaa tctagaagcc cattctggtt gttctg                                36

<210> SEQ ID NO 6
<211> LENGTH: 36
<212> TYPE: DNA
<213> ORGANISM: Artificial Sequence
<220> FEATURE:
<223> OTHER INFORMATION: oligonucleotide

<400> SEQUENCE: 6
acatcacact tctagattta gcgagccacg ttttct                                36

<210> SEQ ID NO 7
<211> LENGTH: 761
<212> TYPE: PRT
<213> ORGANISM: C. neoformans

<400> SEQUENCE: 7
```

| Met | Pro | Ile | Ser | Thr | Leu | Gln | Leu | Lys | Thr | Tyr | Tyr | Pro | Val | Pro | Thr |
|---|---|---|---|---|---|---|---|---|---|---|---|---|---|---|---|
| 1 | | | | 5 | | | | | 10 | | | | | 15 | |

| Pro | Thr | Thr | Met | Ser | Gly | Ile | Gln | Phe | Asp | Val | Ser | Arg | Leu | Cys | Ala |
|---|---|---|---|---|---|---|---|---|---|---|---|---|---|---|---|
| | | | 20 | | | | | 25 | | | | | 30 | | |

| Ala | Thr | Ile | Ser | Ile | Gln | Gly | Arg | His | Phe | Val | Asp | Ser | His | Gly | Arg |
|---|---|---|---|---|---|---|---|---|---|---|---|---|---|---|---|
| | | 35 | | | | | 40 | | | | | 45 | | | |

| Val | Leu | His | Leu | Arg | Gly | Ala | Asn | Val | Ser | Ala | Ala | Ser | Lys | Val | Pro |
|---|---|---|---|---|---|---|---|---|---|---|---|---|---|---|---|
| | 50 | | | | | 55 | | | | | 60 | | | | |

| Ala | Thr | Pro | Ala | Pro | Lys | Ile | His | Asp | His | Ala | Gln | Ala | Ser | Tyr | Val |
|---|---|---|---|---|---|---|---|---|---|---|---|---|---|---|---|
| 65 | | | | | 70 | | | | | 75 | | | | | 80 |

| Gly | Arg | Pro | Phe | Arg | Leu | Glu | Glu | Ala | Asp | Glu | His | Trp | Ala | Arg | Leu |
|---|---|---|---|---|---|---|---|---|---|---|---|---|---|---|---|
| | | | | 85 | | | | | 90 | | | | | 95 | |

| Lys | Ser | Trp | Gly | Leu | Thr | Phe | Val | Arg | Ile | Thr | Val | Thr | Trp | Glu | Ala |
|---|---|---|---|---|---|---|---|---|---|---|---|---|---|---|---|
| | | | 100 | | | | | 105 | | | | | 110 | | |

| Leu | Glu | His | Lys | Glu | Arg | Gly | Val | Tyr | Asp | Glu | Asp | Tyr | Leu | Ala | Tyr |
|---|---|---|---|---|---|---|---|---|---|---|---|---|---|---|---|
| | | 115 | | | | | 120 | | | | | 125 | | | |

| Leu | Arg | Ala | Leu | Leu | Gln | Ser | Met | Glu | Pro | Tyr | Gly | Leu | Val | Ala | Tyr |
|---|---|---|---|---|---|---|---|---|---|---|---|---|---|---|---|
| | 130 | | | | | 135 | | | | | 140 | | | | |

| Ile | Ala | Leu | His | Gln | Asp | Val | Trp | Ser | Arg | Tyr | Cys | Gly | Gly | Ser | Gly |
|---|---|---|---|---|---|---|---|---|---|---|---|---|---|---|---|
| 145 | | | | | 150 | | | | | 155 | | | | | 160 |

| Ala | Pro | Gly | Trp | Thr | Leu | Glu | Ala | Ala | Gly | Phe | Asp | Leu | Ser | Asn | Glu |
|---|---|---|---|---|---|---|---|---|---|---|---|---|---|---|---|
| | | | | 165 | | | | | 170 | | | | | 175 | |

| Gly | Glu | Asn | Leu | Ser | Leu | Ser | Gly | Ala | Ala | Phe | Leu | Asp | Gly | Ile | Lys |
|---|---|---|---|---|---|---|---|---|---|---|---|---|---|---|---|
| | | | 180 | | | | | 185 | | | | | 190 | | |

| Ser | Gly | Arg | Leu | Ala | Gly | Glu | Arg | Gly | Leu | Trp | Pro | Thr | Gly | Tyr | Gln |
|---|---|---|---|---|---|---|---|---|---|---|---|---|---|---|---|
| | | 195 | | | | | 200 | | | | | 205 | | | |

| Lys | Leu | Ala | Ala | Ala | Thr | Met | Asn | Thr | Leu | Phe | Trp | Gly | Gly | Glu | Thr |
|---|---|---|---|---|---|---|---|---|---|---|---|---|---|---|---|
| | 210 | | | | | 215 | | | | | 220 | | | | |

```
Phe Ala Pro Leu Leu Lys Val Pro Gly Gln Ile Asp Gly Lys Trp Val
225                 230                 235                 240

Ser Arg Asn Ile Gln Val Tyr Leu Gln Glu Ala Phe Leu Ala Ala Thr
            245                 250                 255

Ala Lys Leu Val Lys Ala Val Gly Asp Leu Glu Thr Val Met Gly Phe
        260                 265                 270

Glu Leu Met Asn Glu Pro His Pro Gly Phe Ile Gly Ile Gln Ser Ile
    275                 280                 285

His Glu Trp Asp Tyr Thr Thr Asp Leu His Leu Gly Gln Phe Pro Ser
290                 295                 300

Pro Leu Gln Ser Phe Ser Met Gly Ala Gly His Pro Thr Pro Asn Val
305                 310                 315                 320

Pro Val Tyr Thr Arg Ser Phe Pro Phe Pro Thr Arg Val Thr Ser His
            325                 330                 335

Val Thr Ala Asn Pro Glu Gly Ala Cys Ala Trp Ala Ser Lys Glu Cys
        340                 345                 350

Pro Trp Glu Lys His Gly Val Trp Arg Trp Ser Glu Ala Lys Gln Glu
    355                 360                 365

Ala Ala Ala Leu Gln Gln Asp Tyr Phe Val Lys Asn Arg Asp Gly Gly
370                 375                 380

Lys Val Asp Phe Tyr Glu Asp Phe Tyr Phe Pro Phe Val Arg Lys Trp
385                 390                 395                 400

Glu Gln Val Ile Gly Asn Ile Ser Ser Thr Lys Gly Leu Lys Ala
            405                 410                 415

Arg Met Val Glu Ala Ile Pro Asn Glu Leu Cys Pro Glu Trp Lys Glu
        420                 425                 430

Glu Ser Arg Pro Lys Asn Met Val Tyr Ala Pro His Trp Tyr Asp Leu
    435                 440                 445

Asn Thr Leu Phe Lys Lys Lys Phe Gly Phe Met Ser Val Asn Val Gln
450                 455                 460

Gly Leu Ala Arg Gly Met Phe Ile Leu Arg Ala Leu Tyr Phe Gly Thr
465                 470                 475                 480

Ala Ala Ala Lys Ala Asn Tyr Ala Leu Gln Ile Lys Thr Ile Val Leu
            485                 490                 495

Ala Ala Arg Leu Lys Leu Gly Pro Val Pro Val Ile Phe Gly Glu Cys
        500                 505                 510

Gly Val Pro Met Asp Ile Asn Asn Glu Glu Ala Phe Arg Thr Gly Asp
    515                 520                 525

Trp Lys Trp Gln Glu Arg Ser Met Asp Ala Leu Ile Ser Ala Met Glu
530                 535                 540

Gly Ala Leu Met Gly Phe Asn Leu Trp Thr Tyr Asn Pro Ala Asn Arg
545                 550                 555                 560

Asp Asp Ile Gly Asp Asp Trp Asn Ala Glu Asn Phe Ser Trp Tyr Ser
            565                 570                 575

Glu Ser Asn Arg Thr Lys Leu Leu Lys Asn Ala Glu Lys Ser Ser Asp
        580                 585                 590

Gly Leu Asp Val Gly Ala Arg Leu Leu Asn Val Ile Val Arg Pro Tyr
    595                 600                 605

Pro Ile Ala Thr Ala Gly Asn Pro Thr Ser Leu Ala Tyr Asp Ala Asn
610                 615                 620

Ala Cys Ala Phe Thr Tyr Arg Phe Arg Ser Pro Leu Arg Val Ser Ala
625                 630                 635                 640
```

```
Ala Ala Pro Thr Pro Glu Glu Tyr Thr Glu Ile Phe Leu Pro Arg Arg
                645                 650                 655

Val Phe Arg Lys Glu Ser Thr Glu Trp Thr Val Thr Ala Gly Gly Lys
            660                 665                 670

Val His Val Asp Trp Glu Arg Glu Arg Val Phe Val Trp Phe Glu Asp
            675                 680                 685

Ser Ser Leu Thr Ala Ala Ser Ile Lys Asp Asp Thr Arg Pro Arg Arg
        690                 695                 700

Ile Asp Ile Trp Val Ile Gly Arg Lys Val Glu Asn Trp Ser Ile
705                 710                 715                 720

Ala Gln Ile Leu Val Ala Val Ile Leu Leu Leu Gly Val Leu Val
            725                 730                 735

Ala Tyr Tyr Ala Gln Leu Tyr Glu Trp Glu Lys Asp Lys Met Ile Phe
            740                 745                 750

Gln His Leu Arg Glu Ala Asn Gly Met
        755                 760

<210> SEQ ID NO 8
<211> LENGTH: 764
<212> TYPE: PRT
<213> ORGANISM: S. cerevisiae

<400> SEQUENCE: 8

Met Pro Ala Lys Ile His Ile Ser Ala Asp Gly Gln Phe Cys Asp Lys
1               5                   10                  15

Asp Gly Asn Glu Ile Gln Leu Arg Gly Val Asn Leu Asp Pro Ser Val
            20                  25                  30

Lys Ile Pro Ala Lys Pro Phe Leu Ser Thr His Ala Pro Ile Glu Asn
        35                  40                  45

Asp Thr Phe Phe Glu Asp Ala Asp Lys Val Ser Phe Ile Asn His Pro
    50                  55                  60

Leu Val Leu Asp Asp Ile Glu Gln His Ile Ile Arg Leu Lys Ser Leu
65                  70                  75                  80

Gly Tyr Asn Thr Ile Arg Leu Pro Phe Thr Trp Glu Ser Leu Glu His
                85                  90                  95

Ala Gly Pro Gly Gln Tyr Asp Phe Asp Tyr Met Asp Tyr Ile Val Glu
            100                 105                 110

Val Leu Thr Arg Ile Asn Ser Val Gln Gln Gly Met Tyr Ile Tyr Leu
        115                 120                 125

Asp Pro His Gln Asp Val Trp Ser Arg Phe Ser Gly Gly Ser Gly Ala
    130                 135                 140

Pro Leu Trp Thr Leu Tyr Cys Ala Gly Phe Gln Pro Ala Asn Phe Leu
145                 150                 155                 160

Ala Thr Asp Ala Ala Ile Leu His Asn Tyr Tyr Ile Asp Pro Lys Thr
                165                 170                 175

Gly Arg Glu Val Gly Lys Asp Glu Ser Tyr Pro Lys Met Val Trp
            180                 185                 190

Pro Thr Asn Tyr Phe Lys Leu Ala Cys Gln Thr Met Phe Thr Leu Phe
        195                 200                 205

Phe Gly Gly Lys Gln Tyr Ala Pro Lys Cys Thr Ile Asn Gly Glu Asn
    210                 215                 220

Ile Gln Asp Tyr Leu Gln Gly Arg Phe Asn Asp Ala Ile Met Thr Leu
225                 230                 235                 240

Cys Ala Arg Ile Lys Glu Lys Ala Pro Glu Leu Phe Glu Ser Asn Cys
                245                 250                 255
```

-continued

```
Ile Ile Gly Leu Glu Ser Met Asn Glu Pro Asn Cys Gly Tyr Ile Gly
            260                 265                 270

Glu Thr Asn Leu Asp Val Ile Pro Lys Glu Arg Asn Leu Lys Leu Gly
            275                 280                 285

Lys Thr Pro Thr Ala Phe Gln Ser Phe Met Leu Gly Glu Gly Ile Glu
            290                 295                 300

Cys Thr Ile Asp Gln Tyr Lys Arg Thr Phe Phe Gly Phe Ser Lys Gly
305                 310                 315                 320

Lys Pro Cys Thr Ile Asn Pro Lys Gly Lys Lys Ala Trp Leu Ser Ala
                325                 330                 335

Glu Glu Arg Asp Ala Ile Asp Ala Lys Tyr Asn Trp Glu Arg Asn Pro
            340                 345                 350

Glu Trp Lys Pro Asp Thr Cys Ile Trp Lys Leu His Gly Val Trp Glu
            355                 360                 365

Ile Gln Asn Gly Lys Arg Pro Val Leu Leu Lys Pro Asn Tyr Phe Ser
            370                 375                 380

Gln Pro Asp Ala Thr Val Phe Ile Asn Asn His Phe Val Asp Tyr Tyr
385                 390                 395                 400

Thr Gly Ile Tyr Asn Lys Phe Arg Glu Phe Asp Gln Glu Leu Phe Ile
                405                 410                 415

Ile Ile Gln Pro Pro Val Met Lys Pro Pro Asn Leu Gln Asn Ser
            420                 425                 430

Lys Ile Leu Asp Asn Arg Thr Ile Cys Ala Cys His Phe Tyr Asp Gly
            435                 440                 445

Met Thr Leu Met Tyr Lys Thr Trp Asn Lys Arg Ile Gly Ile Asp Thr
450                 455                 460

Tyr Gly Leu Val Asn Lys Lys Tyr Ser Asn Pro Ala Phe Ala Val Val
465                 470                 475                 480

Leu Gly Glu Asn Asn Ile Arg Lys Cys Ile Arg Lys Gln Leu Ser Glu
                485                 490                 495

Met Gln Lys Asp Ala Lys Ser Met Leu Gly Lys Lys Val Pro Val Phe
            500                 505                 510

Phe Thr Glu Ile Gly Ile Pro Phe Asp Met Asp Lys Lys Ala Tyr
            515                 520                 525

Ile Thr Asn Asp Tyr Ser Ser Gln Thr Ala Ala Leu Asp Ala Leu Gly
            530                 535                 540

Phe Ala Leu Glu Gly Ser Asn Leu Ser Tyr Thr Leu Trp Cys Tyr Cys
545                 550                 555                 560

Ser Ile Asn Ser His Ile Trp Gly Asp Asn Trp Asn Asn Glu Asp Phe
                565                 570                 575

Ser Ile Trp Ser Pro Asp Asp Lys Pro Leu Tyr His Asp Thr Arg Ala
            580                 585                 590

Lys Thr Pro Thr Pro Glu Pro Ser Pro Ala Ser Thr Val Ala Ser Val
            595                 600                 605

Ser Thr Ser Thr Ser Lys Ser Gly Ser Ser Gln Pro Pro Ser Phe Ile
            610                 615                 620

Lys Pro Asp Asn His Leu Asp Leu Asp Ser Pro Ser Cys Thr Leu Lys
625                 630                 635                 640

Ser Asp Leu Ser Gly Phe Arg Ala Leu Asp Ala Ile Met Arg Pro Phe
                645                 650                 655

Pro Ile Gln Ile His Gly Arg Phe Glu Phe Ala Glu Phe Asn Leu Cys
            660                 665                 670
```

```
Asn Lys Ser Tyr Leu Leu Lys Leu Val Gly Lys Thr Thr Pro Glu Gln
            675                 680                 685

Ile Thr Val Pro Thr Tyr Ile Phe Ile Pro Arg His His Phe Thr Pro
    690                 695                 700

Ser Arg Leu Ser Ile Arg Ser Ser Gly His Tyr Thr Tyr Asn Thr
705                 710                 715                 720

Asp Tyr Gln Val Leu Glu Trp Phe Glu Pro Gly His Gln Phe Ile
                725                 730                 735

Glu Ile Cys Ala Lys Ser Lys Ser Arg Pro Asn Thr Pro Gly Ser Asp
                740                 745                 750

Thr Ser Asn Asp Leu Pro Ala Glu Cys Val Ile Ser
            755                 760

<210> SEQ ID NO 9
<211> LENGTH: 851
<212> TYPE: PRT
<213> ORGANISM: C. neoformans

<400> SEQUENCE: 9

Met Pro Pro Pro Glu Val Ser Pro Val Thr Gly Asn Pro Val Ser
1               5                   10                  15

Pro His Tyr Ile His Ser Ser Thr Leu His Phe Gln Asp Val Asn Gly
                20                  25                  30

Arg Ser Leu Val Leu Arg Gly Val Asn Leu Ser Gly Ser Ala Lys His
            35                  40                  45

Pro Asn Asn Gln Pro Ser His Ile Arg Glu Gly Phe Trp Glu Thr Ala
    50                  55                  60

Glu Ala Gly Lys Gly Asp Phe Ile Asn Lys Pro Leu Asn Leu Asp Asp
65              70                  75                  80

Gly Ser Ala Asp Leu His Leu Ala Arg Leu Lys Ala Trp Gly Tyr Asn
                85                  90                  95

Leu Leu Arg Tyr Val Phe Thr Trp Glu Ser Leu Glu His Ala Gly Pro
            100                 105                 110

Lys Glu Tyr Asp Tyr Ala Tyr Met Asp Tyr Ile Ile Ala Val Leu Arg
        115                 120                 125

Lys Cys Lys Glu Trp Gly Phe Arg Val Phe Met Asp Pro His Gln Asp
130                 135                 140

Val Trp Ser Arg Phe Thr Gly Gly Ser Gly Ala Pro Leu Trp Thr Leu
145                 150                 155                 160

Tyr Ala Cys Gly Ile Asp Pro Tyr His Leu Thr Ala Thr Ala Ala Ala
                165                 170                 175

Tyr Leu His Cys Glu Trp Pro Ser Ala Glu Ser Pro Lys Pro Gln Asp
            180                 185                 190

Phe Pro Ala Met Ile Trp Gly Thr Asn Tyr Thr His Leu Ala Asn Gln
        195                 200                 205

Thr Ile Trp Thr Phe Phe Phe Ala Gly Lys Thr Tyr Ala Pro Lys Cys
    210                 215                 220

Ile Ile Asp Gly Lys Asn Ile Gln Asp Phe Leu Gln Asp His Phe Ile
225                 230                 235                 240

Asp Ala Val Gly Glu Leu Ala Lys Arg Ile Ala Glu Glu Ala Gly Asp
                245                 250                 255

Leu Leu Asp Glu Cys Val Ile Gly Trp Asp Ser Ile Asn Glu Pro Gly
            260                 265                 270

Glu Gly Leu Ile Gly Cys Lys Asp Leu Ala Val Ile Pro Ala Glu Gln
        275                 280                 285
```

```
Gln Leu Lys Lys Gly Pro Ser Pro Thr Pro Ile Glu Gly Met Arg Leu
290                 295                 300
Gly Met Gly Glu Ala Gln Asp Val Gln Ala Trp Asn Phe Gly Pro Met
305                 310                 315                 320
Gly Pro Tyr Arg Gly Ser Arg Gln Thr Ile Asp Pro Lys Gly Val Lys
            325                 330                 335
Leu Trp Leu Ser Lys Glu Asp Val Lys Arg Gly Ser Gly Lys Trp
            340                 345                 350
Gly Trp Thr Arg Gly Lys Glu Trp Ala Leu Gly Thr Cys Ile Trp Ala
            355                 360                 365
His His Gly Val Trp Glu Ile Ala Thr Ser Thr Leu Leu Arg Pro Asp
370                 375                 380
Tyr Phe Ser Thr Leu Pro Thr Asn Pro Gly His Gln Val Asp Phe Val
385                 390                 395                 400
Asp Asp Phe Trp Ala Leu His Trp Leu Ala Tyr Ser Ser Arg Ile Arg
                405                 410                 415
Leu His His Pro Glu Ser Ile His Phe Ile Gln Ala Pro Val Leu Arg
            420                 425                 430
Gln Pro Pro Lys Leu Pro Glu Ser Phe Leu Lys Gly Arg Ala Cys Ser
            435                 440                 445
Ser Pro His Phe Tyr Asp Gly Leu Thr Leu Met Thr Lys His Trp Asn
450                 455                 460
Trp Phe Asn Ala Asp Ala Ile Gly Val Ile Arg Lys Lys Tyr Trp Ser
465                 470                 475                 480
Ile Val Gln Ala Val Arg Ile Gly Glu Gly Pro Ile Arg Lys Met Ile
                485                 490                 495
Gln Gly Glu Leu Ala Val Leu Lys Gln Asp Thr Ile Asp Ile Leu Gly
            500                 505                 510
Asn Tyr Pro Thr Leu Val Gly Glu Ile Gly Ile Pro Tyr Asp Met Asp
            515                 520                 525
Asp Lys Lys Ala Tyr Gly Tyr Val Asp Gly Gly Arg Gly Glu Gly Asp
            530                 535                 540
Tyr Ser Ser Gln Gln Lys Ala Met Asp Cys Ser Met Asn Ala Cys Asp
545                 550                 555                 560
Gly Pro Asn Cys Leu Asn Tyr Ala Ile Trp Asn Tyr Val Pro Asp Asn
                565                 570                 575
Val His Glu Trp Gly Asp Asn Trp Asn Gly Glu Asp Leu Ser Leu Trp
            580                 585                 590
Ser Val Asp Asp Lys Glu Gln Glu Ser Tyr His Asp Ser Pro Arg Ser
            595                 600                 605
Asp Thr Pro Asn Phe Ser Thr Asn Ser Asn Ser Leu Thr Asn Ser Ser
            610                 615                 620
Ala Thr Leu Thr Val Pro Met Ser Gly Ala Ser Lys Leu Arg Pro Ser
625                 630                 635                 640
Pro Ser Val Ile Asp Ser Gly Asp Phe Ser Pro Thr Leu Ile Leu Asp
                645                 650                 655
Gly Ser Arg Ala Val Ala Phe Cys Arg Pro Tyr Pro Val Ala Thr
            660                 665                 670
Val Gly Ile Pro Glu Arg Ile Asp Phe Asp Ile Thr Ser Thr Lys Phe
            675                 680                 685
Lys Tyr Ala Val Arg Val Arg Ala Asp Asp Ile Ala Asn Glu Gln Val
690                 695                 700
```

```
Tyr Thr Glu Ile Tyr Leu Pro Phe Val His Tyr Ala Ala Ser Leu Asn
705                 710                 715                 720

Ala Ser Arg Ser Ala Gly His Asn Pro Asn Leu Gly Gln Thr Thr Ser
            725                 730                 735

Thr Ser Ala Asp Gly Asp Ser Thr Val Ser Ser Arg Gln Thr Ser
        740                 745                 750

Lys Val Asp Leu Ile Glu Asp Glu Arg Ala Ile Lys Ser Ser Asp Pro
            755                 760                 765

Ser Ser Val Ser Ile Arg Ser Val Pro Tyr Ser Ser Phe Ala Gln Leu
        770                 775                 780

Ser Leu Asp Val Thr Ile Val Ala Ser His Gly Arg Val Glu Ile Gln
785                 790                 795                 800

Gly Gln Thr Leu Arg Trp Trp Tyr Pro Val Pro Gly Thr Gly Glu Glu
            805                 810                 815

Val Tyr Thr Ile Glu Val Gln Arg Asn Gly Gly Ala Leu Arg Arg Asp
            820                 825                 830

Leu Gly Tyr Val Gln Gln Gly Asn Phe Leu Asp Val Cys Pro Glu Cys
        835                 840                 845

Val Ile Ala
    850

<210> SEQ ID NO 10
<211> LENGTH: 897
<212> TYPE: PRT
<213> ORGANISM: C. albicans

<400> SEQUENCE: 10

Met Gln Ser Ala Arg Tyr Ala Ser Glu Leu Ile Gln Asp Arg Ile Ser
1               5                   10                  15

Leu Tyr Ser Ser Ala Ser Ser Val Ser Ile Ser Gly Val Arg Pro Leu
            20                  25                  30

Lys Arg Arg Tyr Ser Pro Gln Gln Ser Ile Gln Pro Thr Asp Thr Thr
        35                  40                  45

Ser Thr Ser Ile Leu Glu Cys Thr Pro Leu Glu Ser Asn Met Lys Gly
    50                  55                  60

Asp Leu Val Asp Lys Lys Thr Gly Arg Lys Val Thr Leu Lys Gly Ile
65              70                  75                  80

Asn Val Asp Ser Gln Met Lys Leu Pro Ala Thr Pro Tyr Met Pro Ser
            85                  90                  95

Tyr Glu Gly Asp Cys Thr Asp Pro Asp Asn Ile Phe Phe Asp Gly Asp
        100                 105                 110

Asn Val Ser Phe Val Gly Arg Pro Phe Pro Leu Gln Glu Ala Arg Met
    115                 120                 125

His Leu Gln Arg Ile Lys Asp Trp Gly Tyr Thr Thr Ile Arg Tyr Leu
    130                 135                 140

Ile Thr Trp Glu Ala Met Glu His Ala Gly Pro Gly Lys Tyr Asp Arg
145                 150                 155                 160

Glu Phe Val Asn Tyr Thr Ile Glu Val Leu Lys Ile Ile Glu Glu Val
            165                 170                 175

Gly Gly Leu Tyr Val Phe Phe Gly Phe His Gln Asp Val Trp Ser Arg
        180                 185                 190

Tyr Ser Gly Gly Ser Gly Ala Pro Met Trp Thr Phe Tyr Ala Ala Gly
    195                 200                 205

Leu Asp Pro Lys Cys Phe Ala Lys Thr Glu Ala Ala Ile Leu His Asn
    210                 215                 220
```

```
Glu Pro Arg Phe His Asp Ser Ser Asp Thr Tyr His Lys Met Leu Trp
225                 230                 235                 240

Thr Ser Asn Tyr Lys Arg Leu Ala Ser Leu Val Met Phe Thr Leu Phe
            245                 250                 255

Phe Ala Gly Lys Ile Tyr Phe Pro Asp Leu Ile Leu Asn Gly Glu Asn
        260                 265                 270

Ile Gln Asp Tyr Leu Gln Asn His Phe Leu Lys Ala Val Glu Phe Leu
    275                 280                 285

Trp Lys Arg Ile Cys Arg Lys Leu Pro Lys Leu Ile Lys Asn Gly Thr
290                 295                 300

Ile Leu Gly Phe Glu Ser Met Asn Glu Pro Asn Ser Gly Leu Ile Gly
305                 310                 315                 320

Tyr Pro Asp Leu Ser Arg Val Pro Asp Tyr Gln Gln Leu Arg Val Gly
            325                 330                 335

Thr Thr Pro Thr Ala Phe Gln Ala Met Lys Leu Gly Met Gly Phe Thr
        340                 345                 350

Cys Glu Val Asp Glu Tyr His Ile Ser Val Thr Gly Pro Arg Lys Thr
    355                 360                 365

Gly Ile Lys Ile Val Asp Pro Lys Gly Ala Arg Ala Trp Ile Ser Arg
370                 375                 380

Ala Thr Ala Gln Lys Ile Asp Lys His Tyr Gly Phe Lys Arg Cys Thr
385                 390                 395                 400

Asp Trp Pro Ile Gly Lys Cys Ile Phe Ala His Lys Gly Ile Trp Lys
            405                 410                 415

Trp Thr Asp Gly Phe Asp Phe Asn Ser Leu Gln Glu Leu Thr Gln Glu
        420                 425                 430

Gln Arg Leu Glu Val Ser Ser Lys Cys Gln Met Leu Asp Pro Glu His
    435                 440                 445

Phe Ser Lys Ser Gln Ser Thr Gly Arg Ile Asp Ala Glu Tyr Phe Val
450                 455                 460

Asn Asn His Phe Val Asp His Tyr Ile Ala Phe Lys Asn Val Val Arg
465                 470                 475                 480

Lys Ile Tyr Pro Asp Ser Phe Val Phe Met Ser Thr Pro Val Leu Glu
            485                 490                 495

Ile Pro Pro Thr Leu Lys Leu Asp Asp Arg Asn Ile Ile Asp Lys Lys
        500                 505                 510

Thr Val Tyr Cys Pro His Tyr Tyr Asp Gly Leu Ser Leu Met Phe Lys
    515                 520                 525

Cys Trp Asn Val Lys Tyr Asn Val Asp Thr Leu Gly Ile Met Arg Asn
530                 535                 540

Arg Tyr Leu Asn Pro Val Leu Gly Ile Val Phe Gly Glu Arg Ala Ile
545                 550                 555                 560

Arg Asn Cys Leu Lys Lys Gln Phe Met Glu Met Arg Asn Glu Cys Asn
            565                 570                 575

Thr His Leu Gly Asn Ile Pro Ile Leu Met Ser Glu Thr Gly Met Pro
        580                 585                 590

Phe Asp Met Asp Arg Lys Arg Ala Tyr Arg Asp Gly Met Phe Asp Ser
    595                 600                 605

Gln Thr Ala Ala Leu Asp Ala Ile Ser Asn Ala Leu Glu Gly Ala Asn
610                 615                 620

Met Ser His Thr Tyr Trp Cys Tyr Asn Ser Ala Asn Asn His Lys Trp
625                 630                 635                 640
```

-continued

```
Gly Asp Asn Trp Asn Asn Glu Asp Phe Ser Phe Trp Ser Pro Asp Asp
                645                 650                 655

Arg Leu Leu Thr Phe Asp Glu Asp Cys Asn Glu Asn Gln Ser Ile Ser
            660                 665                 670

Ser Arg Arg Arg Arg Arg Ser Phe Lys Lys Asp Pro Arg Thr Ala
        675                 680                 685

Leu Arg Arg Ala Val Val Ala Thr Lys Met Gly Leu Ser Ala Ser Arg
    690                 695                 700

Gly Ser Thr Arg Ser Ala Ala Ser Glu Ser Ser Phe Thr Ser Glu Lys
705                 710                 715                 720

Asp Ser Ser Glu Gly Tyr Glu Ser Asp Asp Thr Ser Ser Gln Cys Ser
                725                 730                 735

Leu Ile Thr Ser His Ser Ser Asn Ile Tyr His Arg Gln Phe Lys Lys
            740                 745                 750

Cys Tyr Pro Ser Pro Asp Gly Val Arg Ala Val Ser Ala Thr Ile Arg
        755                 760                 765

Pro Tyr Leu Met Ala Thr Lys Gly Ser Val Val Ala Val Glu Phe Asp
    770                 775                 780

Ile Lys Ser Val Lys Tyr Ser Leu Ser Leu Ser Ile Asp Lys Ser Asp
785                 790                 795                 800

Leu Ser Leu Glu Thr Thr Pro Ser Ile Ile Phe Val Pro Lys Trp His
                805                 810                 815

Tyr Pro Phe Leu Asp Tyr Gly Asp Ile Tyr Leu Thr Ser Gly Tyr Val
            820                 825                 830

Lys Tyr Asn Glu Glu Leu Gln Tyr Leu Glu Trp Tyr His Ser Arg Asp
        835                 840                 845

Pro Thr Leu Pro Glu Asp Glu Asn Glu Thr Thr Gln Gly Ile Ser Thr
    850                 855                 860

Glu Thr Ile Ile Ile Lys Asn Asn Ser Gly Ser Leu Glu Asp Ser Lys
865                 870                 875                 880

Leu Val Glu Glu Lys Gly Val Phe Gly Asn Glu Ile Gly Cys Pro Val
                885                 890                 895

Thr
```

VACCINE COMPOSITIONS AGAINST PATHOGENIC FUNGI AND METHODS FOR USE THEREOF

CROSS REFERENCE TO RELATED APPLICATION

This application claims the benefit of priority from U.S. Provisional Application No. 62/372,894, filed Aug. 10, 2016, the entire contents of which are incorporated herein by reference.

STATEMENT REGARDING FEDERALLY SPONSORED RESEARCH

This invention was made with government support under AI056168, RI071142, and AI125770 awarded by the National Institutes of Health. The government has certain rights in the invention.

INCORPORATION BY REFERENCE OF SEQUENCE LISTING

The Sequence Listing in an ASCII text file, 33936_Seq_ST25.txt of 29 KB, created on Aug. 9, 2017, and submitted to the United States Patent and Trademark Office via EFS-Web, is incorporated herein by reference.

BRIEF DESCRIPTION

The present disclosure provides compositions comprising mutant fungi that lack the sterylglucosidase enzyme. This disclosure further provides vaccine compositions effective against pathogenic fungi, comprising a mutant fungus lacking the sterylglucosidase enzyme, as well as methods for isolating sterylglucosides using the mutant fungus compositions of the instant application.

BACKGROUND

The human fungal pathogen *Cryptococcus neoformans* is an opportunistic fungal pathogen and the causative agent of the disease cryptococcosis. *Cryptococcus neoformans* is able to rapidly and effectively adapt to varying conditions, favoring its survival in the environment and in the infected host. Infections caused by *Cryptococcus neoformans* and *Cryptococcus gattii* lead to more than 600,000 deaths per year (Park et al., 2009), especially among immunocompromised individuals. *Cryptococcus neoformans* is the leading cause of fungal meningitis worldwide. In addition to afflicting the central nervous system, *Cryptococcus neoformans* can cause significant damage to most major organ systems including the heart, kidney and liver. Patients at particular risk are those with HIV/AIDS, autoimmune disorders, long term steroid treatments, and patients undergoing solid organ or bone marrow transplantation. Importantly, some species of *Cryptococcus gattii* have been shown to infect also immunocompetent subjects, causing mild to lethal pneumonia.

Many microbial phenotypes have been specifically correlated with virulence in these opportunistic pathogens, such as capsule production, melanin formation, and the secretion of various proteins. Additionally, cellular features such as the cell wall and morphogenesis play important roles in the interaction of *Cryptococcus* with host immune recognition and response pathways.

Despite its significant public health burden, no vaccines currently exist in the clinic for cryptococcosis (or other fungal infections Nanjappa and Klein, 2014). Although experimental vaccines have been developed using the glucuronoxylomannan (GXM) capsule bound to tetanus toxoid (Devi et al., 1991; Casadevall et al., 1992; Devi, 1996), these formulations have not been translated to the clinic and have suffered from drawbacks such as inducing detrimental antibodies in mice (Casadevall and Pirofski, 2005; Datta and Pirofski, 2006). Recent attempts in the mouse models of cryptococcosis have been focused on the use of genetically engineered *C. neoformans* strains that generate cytokines (Wormley et al., 2007; Wozniak et al., 2011) or protein preparations from *C. gattii* administered prior to infection (Chaturvedi et al., 2014). Although these attempts have provided valuable insights, studies are still limited and shortcomings exist. For example, complete immunity against *C. gattii* (responsible for severe infections in the USA; Datta et al., 2009; Walraven et al., 2011) has not been achieved (Chaturvedi et al., 2014) demonstrating the need for the development of more effective vaccines against fungal infections.

SUMMARY OF THE DISCLOSURE

In one aspect, this disclosure provides a composition comprising a mutant fungus, wherein said mutant fungus comprises an inactivated Sterylglucosidase (Sgl1) gene or homolog thereof.

Another aspect of this invention is directed towards a vaccine comprising an effective amount of a mutant fungus comprising an inactivated Sterylglucosidase (Sgl1) gene homolog. In some embodiments, the effective amount for the mutant pathogenic fungi is between $1\times10^4$ fungal cells and $5\times10^5$ fungal cells per administration. In a specific embodiment, the vaccine is an inactivated vaccine.

In some embodiments, the vaccine provides protection against pathogenic fungal infections. In a specific embodiment, pathogenic fungal infections the vaccine protects against comprise infections by fungi of genus selected from the group consisting of *Cryptococcus*, *Aspergillus*, and *Candida*. In a specific embodiment, the pathogenic fungal infections comprise infections caused by dimorphic fungi selected from the group consisting of *Coccidioides immitis, Paracoccidioides brasiliensis, Candida albicans, Ustilago maydis, Blastomyces dermatitidis, Histoplasma capsulatum, Sporothrix schenckii,* and *Emmonsia* sp.

Another aspect of this application provides a pharmaceutical composition comprising the vaccine of claim 7 and a pharmaceutically acceptable carrier.

A different aspect of this disclosure provides a method for producing sterylglucosides comprising: providing a mutant fungus comprising an inactivated Sterylglucosidase (Sgl1) gene or homolog thereof; expressing said mutant fungus in a fungal cell, wherein said fungal cell produces sterylglucosides; and isolating said sterylgucosides.

In some embodiments, the mutant fungus of this disclosure lacks the ability to metabolize sterylglucosides (SGs). In some embodiments, the mutant fungus accumulates sterol glycosides.

In some embodiments, the mutant fungus is avirulent.

In some embodiments, the fungus is from a *Cryptococcus* genus. In a specific embodiment, said mutant fungus is selected from the group consisting of *Cryptococcus neoformans, Cryptococcus gatii, Cryptococcus albidus, Crypto-* coccus uniguttulatus, Candida albicans, Aspergillus fumigatus and other fungi in which the Sgl1 gene or homolog thereof is deleted.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A-1E. CNAG_05607 enzyme has sterylglucosidase and not glucosylceramidase activity. (A) *Cryptococcus neoformans* CNAG_05607 (Cn 5607) metabolizes plants SGs in a dose dependent manner and (B) metabolizes SGs extracted from Cn cells (Cn SGs). (C) pH dependence of Cn 5607 activity, as measured based on its ability to cleave plants SGs and produce free sterols, showed maximal activity at pH 4.5. Results are based on the measurement of free sterols performed by liquid chromatography-mass spectrometry (LC-MS). Cn 5607 does not metabolize *C. neoformans* GlcCer (Cn GlcCer) as analyzed by (D) thin layer chromatography (TLC) or by (E) LC-MS (Cerezyme is an analog of the human enzyme β-glucocerebrosidases, and was used as a positive control). Cn 5607 is the endoglycoceramidase-related protein 2 (EGCrP2) also identified by Watanabe et al. (2015). Empty V, empty vector.

FIG. 2A-2H. Deletion of SGL1 causes accumulation of SGs and not GlcCer. Analysis of sterylglucosides (SGs) and glucosylceramide (GlcCer) was performed by (A) TLC and (B-D) gas chromatography-(E-Gmass spectrometry. Results show that the Δsgl1 mutant dramatically accumulates SGs (A,B-D), which are normally undetectable in wild-type (WT) or reconstituted strain (Δsgl1+SGL1). In contrast, the level of GlcCer (A,E-G) in the Δsgl1 mutant is identical to the one observed in the WT or Δsgl1+SGL1 reconstituted strain. Chromatograms are representatives of three separate experiments showing similar results. Peaks denote: (1) Dehydroergosteryl-β-D-glucoside*; (2) Ergosteryl-β-D-glucoside; (3) Ergosta-7,22-dien-3-oyl-β-D-glucoside*; (4) Fecosteryl-β-D-glucoside*; (5) Episteryl-β-D-glucoside*; (6) Lanosteryl-β-D-glucoside* (*: putative structures). (H) Structure and electron-impact (EI) mass spectrum of peak number 2.

FIG. 3A-3C. Deletion of the SGL1 gene in *C. neoformans* abolishes virulence. (A) Virulence studies showed that 100% of mice infected with Δsgl1 survived the infection whereas mice infected with *C. neoformans* WT H99 or with Δsgl1+SGL1 reconstituted strain succumbed to infection within 24±6 and 21±7 days, respectively; n=8 mice in each group. (B) Lung tissue burden analysis showed that the Δsgl1 mutant is eliminated from the lungs after 14 days of inoculation; n=3 mice each at time point. (C) Brain tissue burden analysis showed that Δsgl1 is not found in the brain at anytime during the course of experiment; n=3 mice at each time point.

FIG. 4A-4D. Vaccination studies. (A) Mice were "pre-treated" with Δsgl1 and, after 30 days (time 0), challenged with a lethal dose of *C. neoformans* wild-type H99 (Cn WT) or *Cryptococcus gattii* WT R265 (Cg 265). Mice exposed to Δsgl1 remained alive during the course of experiment (80 days post-infection) whereas all mice that were not exposed to Δsgl1 but to vehicle (PBS) or to the Δgcs1 mutant strain and then challenged with Cn WT succumbed to infection within 35 days; n=8 mice in each group. (B) Pre-treatment with Δsgl1 completely protected $CD4^+$ T-cell depleted mice from a subsequent lethal challenge with *C. neoformans* wild-type H99 (WT); n=8 mice in each group. Depletion of $CD4^+$ was achieved by administering anti-CD4 (Ab) weekly during the entire course of the experiment. The depletion was confirmed by flow cytometry performed at the day of Cn challenge (C-D). Results are representative of three separate experiments showing similar results.

FIG. 5. Alignment of the entire protein sequences of *C. neoformans* protein EGCrP1 (SEQ ID NO: 7), *C. neoformans* protein Sgl1 (SEQ ID NO: 9), *S. cerevisiae* protein Egh1 (SEQ ID NO: 8) and *C. albicans* protein Sgl1 ((SEQ ID NO: 10)). Identical conserved residues are shown in red, homologous residues in at least 3 of the sequences are shown in yellow. The protein homology scores were 45% for *C. neoformans* EGCrP1 (SEQ ID NO: 7 and GenBank Acc. No: BAL46040.1) and *C. neoformans* Sgl1 (SEQ ID NO: 9), 42% for *C. neoformans* EGCrP1 and *S. cerevisiae* Egh1 (SEQ ID NO: 8, and GenBank Acc. No: DAA08553.1), and 45% for *C. neoformans* EGCrP1 (SEQ ID NO: 7) and *C. albicans* putative Sgl1 (SEQ ID NO: 10).

FIG. 6. CNAG_05607 enzyme has cholesterol glucosidase activity. The release of cholesterol from cholesterol glycoside by CNAG_05607 enzyme was monitored using GC-MS. Empty vector and Cerezyme were used as negative control. CG, Cholesterol glucoside; Empty V, empty vector.

FIG. 7A-7C. Deletion and reconstitution of the SGL1 gene. (A) Strategy for the deletion of SGL1 in *C. neoformans* wild-type (WT) and creation of the mutant strain Δsgl1. (B) Strategy for the generation of the complemented strain Δsgl1+SGL1. (C) Southern Blot hybridization analysis of genomic DNA of WT, Δsgl1 and Δsgl1+SGL1 digested with ScaI and KpnI and screened with the "SGL1" probe (gray bar in B). Results show that the SGL1 gene has been deleted in the Δsgl1 mutant and reconstituted in the Δsgl1+SGL1 strain. Gene deletion was confirmed using a second probe (5' UTR—black bar in B). 5' UTR, 5' untranslated region; 3' UTR, 3' untranslated region; NAT1, nourseothricin 1; Sgl1, sterylglucosidase 1; HYG. Hygromycin B.

FIG. 8A-8F. Histopathology of brains and lungs obtained from the CBA/J mice infected intranasally with *C. neoformans* wild-type (WT), Δsgl1, and Δsgl1+SGL1 strains. The brains (A, C and E) were stained with mucicarmine stain, the lungs (B, D, and F) were stained with Hematoxylin and Eosin (H&E) stain. Black bar, 50 μm.

FIG. 9A-9J. Characterization of virulence phenotypes in the Δsgl1 mutant strain. (A-B) *C. neoformans* wild-type (WT), Δsgl1, and Δsgl1+SGL1 strains showed identical growth in DMEM at 37° C., 5% CO2 and at pH 7.4 (A) or pH 4 (B). (C) *C. neoformans* cells were plated on medium containing L-DOPA and the melanin produced by WT, Δsgl1, or Δsgl1+SGL1 strain was similar. (D-F) Capule size of WT(D), Δsgl1 (E), or Δsgl1+SGL1 (F) strains was similar when cells were incubated in DMEM at 37° C., 5% CO2. White bar, 10 μm (G) Cell body and capsule size of WT, Δsgl1, or Δsgl1+SGL1 strains, reported by measuring the cell body and capsule size of 50 cells for each strain under the microscope. (H) There were no major differences among WT, Δsgl1, and Δsgl1+SGL1 in their ability to grow under stressed conditions (hydrogen peroxide and nitrosative stress). (I-J) Phagocytosis (I) and intracellular killing (J) within a macrophage-like cell line J774A. 16 was identical between WT, Δsgl1, or Δsgl1+SGL1 strains at 2 and 24 hours, respectively.

FIG. 10. Isolation of sterolglucosides from *Cryptococcus neoformans* Δsgl1. Thin Layer Chromathography (TLC) of sterolglucosides isolated from *Cryptococcus neoformans* and stained with orcinol. Lane 1, sterolglucosides standard from plants; Lane 2, glucosylceramide standard from soy; lane 3; purified sterolglucosides from *C. neoformans.*

DETAILED DESCRIPTION

It has been demonstrated herein that a non-pathogenic (avirulent) mutant strain of pathogenic fungi that lacks the gene to metabolize sterylglucosides (SGs) can be used as a vaccine to protect a host against infection by virulent strains of fungi such as *Cryptococcus* strains (including but not limited to *Cryptococcus neoformans, Cryptococcus gatii, Cryptococcus albidus*, and *Cryptococcus uniguttulatus*), *Aspergillus nidulans, Candida albicans*, and other pathogenic dimorphic fungi (including but not limited to *Coccidioides immitis, Paracoccidioides brasiliensis, Candida albicans, Ustilago maydis, Blastomyces dermatitidis, Histoplasma capsulatum, Sporothrix schenckii*, and *Emmonsia* sp.). Accordingly, the present disclosure is directed to compositions and vaccines comprising a mutant fungus comprising an inactivated Sterylglucosidase (Sgl1) gene homolog (aka. delta SGL1 (Δsgl1)).

A "homolog" means a gene related to a second gene by descent from a common ancestral DNA sequence, therefore, the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95%, 97% or 99%). "Sterylglucosidase (Sgl1) gene homolog" furthermore means that the function is equivalent to the function of the Sterylglucosidase (Sgl1) gene.

The Sterylglucosidase (Sgl1) gene encodes for an enzyme that does not metabolizes long-chain Δ8-C9 methyl glucosylceramides in *Cryptococcus neoformans*. The Sgl1 enzyme only metabolizes short-chain glucosylceramides (e.g. C6-glucosylceramide), which are not physiologically relevant because these species of glucosylceramides are not synthesized in fungal cells. Sterylglucosidase (Sgl1) gene homologs encode an enzyme with sterylglucosidase activity (i.e., the ability to metabolize sterolglycosides). BLAST database searches with either the nucleotide sequence of *Cryptococcus neoformans* Sterylglucosidase (Sgl1) gene or with the amino acid sequence of the Sgl1 gene provide other homolog genes and proteins in other fungi species. For example, a BLAST search of CNAG_05607 in *Saccharomyces* genome database reveals a homolog gene called YIR007W in *Saccharomyces cerevisiae*. In addition, protein alignments reveals similarities between Sgl1 homologs from different species (FIG. 5). Protein homology scores was 45% for *C. neoformans* EGCrP1 and *C. neoformans* Sgl1, 42% for *C. neoformans* EGCrP1 and *S. cerevisiae* Egh1, and 45% for *C. neoformans* EGCrP1 and *C. albicans* putative Sgl1.

In some embodiments, the inactivation of the Sterylglucosidase (Sgl1) gene includes a deletion of the whole or a part of the gene such that no functional protein product is expressed (also known as gene knock out). The inactivation of a gene may include a deletion of the promoter or the coding region, in whole or in part, such that no functional protein product is expressed. In other embodiments, the inactivation of Sterylglucosidase (Sgl1) includes introducing an inactivating mutation to the gene, such as an early STOP codon in the coding sequence of the gene, such that no functional protein product is expressed. Deletion or inactivation of the Sterylglucosidase (Sgl1) gene leads to significant accumulation of sterol-glucosides in cells. Sterolglucosides are molecules which are undetectable in wild-type fungi strains. Sterolglucosides accumulated by the mutant fungi trigger host immune responses against pathogenic fungi and help protect from, and prevent against fungal infections.

In some embodiments, gene inactivation is achieved using available gene targeting technologies in the art. Examples of gene targeting technologies include the Cre/Lox system (described in Kühn, R., & M. Torres, R., *Transgenesis Techniques: Principles and Protocols*, (2002), 175-204), homologous recombination (described in Capecchi, Mario R. *Science* (1989), 244: 1288-1292), TALENs (described in Sommer et al., *Chromosome Research* (2015), 23: 43-55, and Cermak et al., *Nucleic Acids Research* (2011): gkr218), and CRISPR Cas system as described in Ran F A et al., *Nature Protocols* (2013).

In one embodiment, Sterylglucosidase (Sgl1) inactivation is achieved by biolistic transformation, which is a gene targeting systems well known in the art with reagents and protocols readily available (Toffaletti et al., *Journal of Bacteriology,* 175.5 (1993): 1405-1411).

Inactivation of the Sterylglucosidase (Sgl1) gene also causes the fungus to become avirulent (non-pathogenic).

As used herein, "pathogenic" means causing symptoms of a disease associated with the pathogen. As used herein "a non-pathogenic strain" or "an avirulent strain" is a strain of microorganism which has the ability to colonize and replicate in an infected individual, but which does not cause disease symptoms associated with virulent strains of the same species of microorganism. The microbe may belong to a genus or even a species that is normally pathogenic but must belong to a strain that is avirulent. Avirulent strains are incapable of inducing a full suite of symptoms of the disease that is normally associated with its virulent pathogenic counterpart. Avirulent strains of microorganisms may be derived from virulent strains by mutation.

In some embodiments, the mutant fungus is from the *Cryptococcus* genus. In other embodiments, the mutant fungus can be from any one of the following *Cryptococcus* fungal strains: *Cryptococcus neoformans, Cryptococcus gatii, Cryptococcus albidus*, and *Cryptococcus uniguttulatus.*

In one embodiment, the mutant fungus comprises an inactivated Sterylglucosidase (Sgl1) gene homolog that can be included in a pharmaceutical composition. As used herein, a pharmaceutical composition is a formulation which contains at least one active ingredient as well as, for example, one or more excipients, buffers, carriers, stabilizers, preservatives and/or bulking agents, and is suitable for administration to a patient to achieve a desired effect or result. The pharmaceutical compositions disclosed herein can have diagnostic, preventative (i.e., phrophylactic), cosmetic and/or research utility in various species, such as for example in human patients or subjects.

This disclosure also provides a composition comprising a combination as described above and a pharmaceutically acceptable carrier. For the purposes of this disclosure, "pharmaceutically acceptable carriers" means any of the standard pharmaceutical carriers. Examples of suitable carriers are well known in the art and may include, but are not limited to, any of the standard pharmaceutical carriers such as a phosphate buffered saline solution and various wetting agents. Other carriers may include additives used in tablets, granules and capsules, and the like. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

The pharmaceutical preparations of the present disclosure can be made up in any conventional form including, inter alia: (a) a solid form for oral administration such as tablets, capsules (e.g. hard or soft gelatin capsules), pills, cachets, powders, granules, and the like; (b) preparations for topical administrations such as solutions, suspensions, ointments, creams, gels, micronized powders, sprays, aerosols and the like. The pharmaceutical preparations may be sterilized and/or may contain adjuvants such as preservatives, stabilizers, wetting agents, emulsifiers, salts for varying the osmotic pressure and/or buffers.

The pharmaceutical compositions of the present disclosure can be used in liquid, solid, tablet, capsule, pill, ointment, cream, nebulized or other forms as explained below. In some embodiments, the composition of the present disclosure can be administered by different routes of administration such as oral, oronasal, parenteral or topical.

"Oral" or "peroral" administration refers to the introduction of a substance, such as a vaccine, into a subject's body through or by way of the mouth and involves swallowing or transport through the oral mucosa (e.g., sublingual or buccal absorption) or both.

"Oronasal" administration refers to the introduction of a substance, such as a vaccine, into a subject's body through or by way of the nose and the mouth, as would occur, for example, by placing one or more droplets in the nose. Oronasal administration involves transport processes associated with oral and intranasal administration.

"Parenteral administration" refers to the introduction of a substance, such as a vaccine, into a subject's body through or by way of a route that does not include the digestive tract. Parenteral administration includes subcutaneous administration, intramuscular administration, transcutaneous administration, intradermal administration, intraperitoneal administration, intraocular administration, and intravenous administration. For the purposes of this disclosure, parenteral administration excludes administration routes that primarily involve transport of the substance through mucosal tissue in the mouth, nose, trachea, and lungs.

Formulations suitable for parenteral administration comprise a composition comprising a mutant fungus comprising an inactivated Sterylglucosidase (Sgl1) gene homolog in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a composition comprising a mutant fungus comprising an inactivated Sterylglucosidase (Sgl1) gene homolog, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered formulation is accomplished by dissolving or suspending the composition comprising a mutant fungus comprising an inactivated Sterylglucosidase (Sgl1) gene homolog in an oil vehicle.

Injectable depot forms are made by forming microencapsule matrices of a composition comprising a mutant fungus comprising an inactivated Sterylglucosidase (Sgl1) gene homolog or in biodegradable polymers such as polylactide-polyglycolide. Depending on the ratio of the composition comprising a mutant fungus comprising an inactivated Sterylglucosidase (Sgl1) gene homolog to polymer, and the nature of the particular polymer employed, the rate of drug release can be controlled. Examples of other biodegradable polymers include poly (orthoesters) and poly (anhydrides). Depot injectable formulations are also prepared by entrapping a composition comprising a mutant fungus comprising an inactivated Sterylglucosidase (Sgl1) gene homolog in liposomes or microemulsions which are compatible with body tissue.

"Topical administration" means the direct contact of a substance with tissue, such as skin or membrane, particularly the oral or buccal mucosa.

For topical administration to the skin or mucous membrane the aforementioned composition is preferably prepared as ointments, tinctures, creams, gels, solution, lotions, sprays; aerosols and dry powder for inhalation, suspensions, shampoos, hair soaps, perfumes and the like. In fact, any conventional composition can be utilized in this invention. Among the preferred methods of applying the composition containing the agents of this invention is in the form of an ointment, gel, cream, lotion, spray; aerosol or dry powder for inhalation. The pharmaceutical preparation for topical administration to the skin can be prepared by mixing the aforementioned active ingredient with non-toxic, therapeutically inert, solid or liquid carriers customarily used in such preparation. These preparations generally contain 0.01 to 5.0 percent by weight, or 0.1 to 1.0 percent by weight, of the active ingredient, based on the total weight of the composition.

In preparing the topical preparations described above, additives such as preservatives, thickeners, perfumes and the like conventional in the art of pharmaceutical compounding of topical preparation can be used. In addition, conventional antioxidants or mixtures of conventional antioxidants can be incorporated into the topical preparations containing the aforementioned active agent. Among the conventional antioxidants which can be utilized in these preparations are included N-methyl-a-tocopherolamine, tocopherols, butylated hydroxyanisole, butylated hydroxytoluene, ethoxyquin and the like.

Cream-based pharmaceutical formulations containing the active agent, used in accordance with this invention, are composed of aqueous emulsions containing a fatty acid alcohol, semi-solid petroleum hydrocarbon, ethylene glycol and an emulsifying agent.

Ointment formulations containing the active agent in accordance with this invention comprise admixtures of a semi-solid petroleum hydrocarbon with a solvent dispersion of the active material. Cream compositions containing the active ingredient for use in this invention preferably comprise emulsions formed from a water phase of a humectant, a viscosity stabilizer and water, an oil phase of a fatty acid alcohol, a semi-solid petroleum hydrocarbon and an emulsifying agent and a phase containing the active agent dispersed in an aqueous stabilizer-buffer solution. Stabilizers may be added to the topical preparation. Any conventional stabilizer can be utilized in accordance with this invention. In the oil phase, fatty acid alcohol components function as a stabilizer. These fatty acid alcohol components function as a stabilizer. These fatty acid alcohol components are derived from the reduction of a long-chain saturated fatty acid containing at least-14 carbon atoms. The ointments, pastes, creams and gels may contain, in addition to a mutant fungus comprising an inactivated Sterylglucosidase (Sgl1) gene homolog, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a composition comprising a mutant fungus comprising an inactivated Sterylglucosidase (Sgl1) gene homolog, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. Also, conventional perfumes and lotions generally utilized in topical preparation for the hair can be utilized in accordance with this invention. Furthermore, if desired, conventional emulsifying agents can be utilized in the topical preparations of this invention.

An oral dosage form comprises cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, or capsules of hard or soft gelatin, methylcellulose or of another suitable material easily dissolved in the digestive tract, each containing a predetermined amount of a composition comprising a mutant fungus comprising an inactivated Sterylglucosidase (Sgl1) gene homolog as an active ingredient. Each tablet, pill, sachet or capsule can preferably contain from about $1\times10^1$ to about $1\times10^9$ cells of mutant fungi as active ingredient. The oral dosages contemplated in accordance with the present invention will vary in accordance with the needs of the individual patient as determined by the prescribing physician.

A compound may also be administered as a bolus, electuary, or paste.

In solid dosage forms for oral administration (e.g., capsules, tablets, pills, dragees, powders, granules and the like), a composition comprising a mutant fungus comprising an inactivated Sterylglucosidase (Sgl1) gene homolog is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a composition comprising a mutant fungus comprising an inactivated Sterylglucosidase (Sgl1) gene homolog therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the composition comprising a mutant fungus comprising an inactivated Sterylglucosidase (Sgl1) gene homolog only, or preferentially, in a certain portion of the gastrointestinal tract, optionally, in a delayed manner. Examples of embedding compositions which can be used include polymeric substances and waxes. The composition comprising a mutant fungus comprising an inactivated Sterylglucosidase (Sgl1) gene homolog can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to a composition comprising a mutant fungus comprising an inactivated Sterylglucosidase (Sgl1) gene homolog, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to a composition comprising a mutant fungus comprising an inactivated Sterylglucosidase (Sgl1) gene homolog, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compositions comprising a mutant fungus comprising an inactivated Sterylglucosidase (Sgl1) gene homolog with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Compositions comprising a mutant fungus comprising an inactivated Sterylglucosidase (Sgl1) gene homolog can be alternatively administered by aerosol. For example, this can be accomplished by preparing an aqueous aerosol, liposomal preparation or solid particles containing a composition comprising a mutant fungus comprising an inactivated Sterylglucosidase (Sgl1) gene homolog preparation. A nonaqueous (e.g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants, innocuous proteins like serum albumin, sorbitan esters, oleic acid, lecithin, amino acids such as glycine, buffers, salts, sugars or sugar alcohols. Aerosols generally are prepared from isotonic solutions.

In another embodiment, said pharmaceutical composition comprising the mutant fungus comprising an inactivated Sterylglucosidase (Sgl1) gene homolog is included in a vaccine composition. Said vaccine composition may be administered by any one of the routes of administration described above.

In one embodiment, the vaccine composition of the present disclosure is an attenuated vaccine comprising a mutant fungus comprising an inactivated Sterylglucosidase (Sgl1) gene homolog (Δsgl1). An attenuated vaccine is a vaccine created by reducing the virulence of a pathogen, but still keeping it viable (or "live"). Attenuation takes an infectious agent and alters it so that it becomes harmless or less virulent.

In another embodiment the vaccine composition of the present disclosure is an inactivated vaccine comprising a mutant fungus comprising an inactivated Sterylglucosidase (Sgl1) gene homolog (delta Sgl1). An inactivated vaccine (or killed vaccine) is a vaccine consisting of virus particles, bacteria, or other pathogens that have been grown in culture and then killed using a method such as heat or formaldehyde. In contrast, live vaccines (which are nearly always attenuated vaccines) use pathogens that are still alive (but are almost always attenuated, that is, weakened). Pathogens for inactivated vaccines are grown under controlled conditions and are killed as a means to reduce infectivity (virulence) and thus prevent infection from the vaccine.

In yet another embodiment, the vaccine composition may further comprise an appropriate adjuvant. Appropriate adjuvants include but are not limited to aluminum hydroxide, aluminum phosphate, gamma inulin, algammulin (a combination of aluminum hydroxide and gamma inulin), cholecalciferol in oil, an oil in water emulsion OWEM1, containing squalene, tween-80, Span-85 in 10 mM phosphate-citrate buffer, oil in water emulsion OWEM2 containing squalene, tween-80, Span-85, alpha tocopherol in phosphate-citrate buffer, and saponin. The saponin-based adjuvants include but are not limited to QS21, QuilA, tomatine, ISCOMs, ISCOMATRIX and GPI-0100. In an embodiment, the range of QS21 is from about 25 to 200 μg. In another embodiment, the QS21 is about 100 μg. In a separate embodiment, the adjuvant is GPI-0100 and the range is from about 1 to 25 mg. In yet another embodiment, GPI-0100 is about 10 mg.

In one embodiment of the disclosure, the vaccine composition is delivered to a subject in a pharmaceutically effective dose. The term "pharmaceutically effective dose" as used herein refers to the amount of the vaccine preparation, which is effective for producing a desired vaccinal effect. As is known in the art of pharmacology, the precise amount of the pharmaceutically effective dose of a vaccine preparation that will yield the most effective results in terms of efficacy of administration of the composition in a given subject will depend upon, for example, the activity, the particular nature, pharmacokinetics, pharmacodynamics, and bioavailability of a particular vaccine preparation, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, to name a few. However, the above guidelines can be used as the basis for fine-tuning the treatment, e.g., determining the optimum dose of administration, which will require no more than routine experimentation consisting of monitoring the subject and adjusting the dosage. Remington: The Science and Practice of Pharmacy (Gennaro ed. 20th edition, Williams & Wilkins Pa., USA (2000)).

In one embodiment, the vaccine comprises about $1\times10^1$, $1\times10^2$, $1\times10^3$, $1\times10^4$, $1\times10^5$, $1\times10^6$, $1\times10^7$, $1\times10^8$, $1\times10^9$ or more mutant fungi cells per administration dose.

In one embodiment, an SGL1 deletion mutant of a fungus (delta SGL1) is used for purification of sterylglucosides. In another embodiment, the mutant fungus is from *Cryptococcus* genus. In yet another embodiment, the *Cryptococcus* fungus is selected from the group consisting of *Cryptococcus neoformans, Cryptococcus gatii, Cryptococcus albidus*, and *Cryptococcus uniguttulatus*. Here, it has been discovered that when the SGL1 gene homolog is deleted in these fungi, sterylglucosides (SGs) begin to accumulate. SGs can be isolated with known biochemical methods in the art.

In another aspect of the present disclosure, mutant fungi exhibiting an inactivated sterylglucosidase enzyme can be used to produce sterylglucoside(s). Specifically, fungal sterylglucosides. Here, a mutant fungi composition including an inactivated SGL1 gene or homolog thereof can be provided and expressed in a cell or collection of cells such as, for example, bacterial cell, fungal cell, yeast cell, or other cell known by those of ordinary skill in the art to be used in protein production. In certain embodiments, the mutant fungi composition is expressed in cells by transfection of the cells with a plasmid or vector that includes the mutant fungi comprising an inactivated SGL1 gene or homolog thereof. The cells can then be grown for a period of time sufficient to express sterolglucoside(s) due to the inactivity of the sterolglucosidase exhibited by the mutant fungi composition. For example, the cells can be grown for at least 1 hour. In other embodiments, the cells can be grown for at least 24 for ours. In another embodiment the cells can be grown for period of time from 1 to 72 hours or greater. In other embodiments, the cells can be grown until a detectable amount of fungal sterolglucoside is detected in the cells.

In a specific embodiment, the cell expressing the mutant fungi is a fungal cell or fungal strain. Non-limiting examples of such fungal cells include *Cryptococcus neoformans*, *Cryptococcus gatii*, *Cryptococcus albidus*, *Cryptococcus uniguttulatus*, *Aspergillus nidulans*, *Candida albicans*. In other embodiments the fungal cells are *Coccidioides immitis*, *Paracoccidioides brasiliensis*, *Candida albicans*, *Ustilago maydis*, *Blastomyces dermatitidis*, *Histoplasma capsulatum*, *Sporothrix schenckii*, or *Emmonsia* sp.

The expression of the mutant fungi of the present disclosure leads to significant accumulation of sterolglucosides in the cells, which can then be isolated and purified, as defined in further detail herein.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Materials and Methods

Strains, Plasmid, and Culture Conditions

The fungal strains used in this study were *C. neoformans* (Cn) var. *grubii* strain H99 wild-type (WT) and *C. gattii* strain R265 and *Saccharomyces cerevisiae* ΔYIR007W mutant (ScΔYIR) derived from BY4741. Bacterial strain *Escherichia coli* DH5-α (Life Technologies, Carlsbad, Calif., USA) was used as competent cells. The plasmid pCR II-TOPO 4.0 kb was used for cloning, and pYES2/CT was used for expression of Cn 5607 in ScΔYIR.

Bacterial strains were grown at 37° C. in Luria-Bertani medium with 75 mg/L of ampicillin. Cn strains were routinely grown in YPD broth at 30° C. and 0.04% atmospheric $CO_2$ for 20-22 h with shaking at 250 rpm. Dulbecco's modified eagle media (DMEM) buffered with 25 mM HEPES and 2% glucose at pH 7.4 or pH 4 was used for growing Cn at 37° C. and 5% $CO_2$ (i.e., physiologically relevant conditions). ScΔYIR strain transformed with pYES2/CT or pYES2/CT– Cn 5607, was grown in yeast nitrogen base (YNB) without amino acids, 1.2 g/L amino acid mixture lacking uracil (ura-), and 2% glucose or 2% galactose (48 h) at 30° C. to induce Cn 5607 expression.

Expression of Cn 5607 in *S. cerevisiae*

Cn 5607 was identified by blasting the Cn WT endoglycoceramidase-related Protein 1 (EGCrP1) sequence in Cn WT Broad Institute genome database [http://www.broadinstitute.org/annotation/genome/cryptococcus_neoformans/MultiHome.html]. Two sequences were found: one 100% identical to EGCrP1 and another one with an E-value of 9e-57, located on chromosome 14 (Cn 5607). To express Cn 5607 in *S. cerevisiae* strains, total RNA was extracted from Cn and the cDNA was synthesized from 1 μg of the total RNA using SuperScript III RNase H-Reverse Transcriptase (Life Technologies). PCR was performed using the cDNA as a template and the following expression primers: PRSGL1-5' forward (5'-GAGCTCATGCCTCCTCCACCAGAAGT-3') (SEQ ID NO: 1) and PRSGL1-5' reverse (5'-TCTAGAAGCAATAACGCATTCAGGACA-3') (SEQ ID NO: 2) carrying the restriction enzyme sites for SacI and XbaI respectively. A 2,556-pb fragment was cloned into pCR II-TOPO vector generating plasmid pCR-Cn 5607 and sequenced. After digestion with SacI and XbaI, Cn 5607 was inserted into pYES2/CT vector generating pYES2/CT-Cn 5607. ScΔYIR was grown in YNB medium overnight at 30° C. and transformed with pYES2/CT empty-vector or pYES2/CT-Cn 5607 using lithium acetate transformation, as previously described (Kawai et al., 2010). After transformation, cells were plated on YNB ura-plates and incubated for 2-3 days in 30° C. incubator. Then, *S. cerevisiae* colonies were patched with sterile toothpicks to fresh YNB ura-plates. To verify the expression of Cn 5607, one single colony containing pYES2/CT or pYES2/CT-Cn 5607 construct was inoculated into 10 ml of YNB ura-containing 2% of glucose and was grown overnight at 30° C. with shaking. The cells were washed twice with PBS 1× and a suitable amount of overnight culture necessary to obtain an $OD_{600}$ of 0.4 was transferred to a fresh YNB ura-medium containing 2% of galactose (induction medium) and incubated for 48 h at 30° C. with shaking. After 48 h, the cells were washed and harvested by centrifugation at 3000 g for 5 min at 4° C., and the cell pellets was stored at −80° C. until ready to be used.

Total proteins were extracted from *S. cerevisiae* strains as previously described in Singh et al., 2011, the entire contents of which is expressly incorporated herein by reference. Protein content was assessed by the method of Bradford using bovine serum albumin (Sigma-Aldrich, St. Louis, Mo., USA) as a standard. Fifty micrograms of *S. cerevisiae* proteins were loaded onto SDS-PAGE and stained with Coomassie Brilliant Blue. Western Blot was used to detect the expression of recombinant fusion protein using Anti-His (C-term)-HRP antibody.

In Vitro Activity Assay of Cn 5607 Using Standard Plants SGs and Purified Cn SGs The in vitro Cn 5607 enzymatic assay was performed using 20 μg of standard SGs (purified from plants and commercially available) or 10 μg of endogenously purified SGs as substrate and ScΔYIR+empty vector or ScΔYIR-Cn 5607 as source of enzyme. The decrease in the intensity of the SGs band was monitored by thin layer chromatography (TLC). Plants SGs were incubated with 200 μg of ScΔYIR+empty vector or 50, 100, and 200 μg of ScΔYIR-Cn 5607 at 30° C. for 1 h. Endogenously purified Cn SGs were incubated with 200 μg of ScΔYIR+empty vector or 100 μg of ScΔYIR-Cn 5607 at 30° C. for 1 h. The reactions were terminated by the addition of 300 μl of $CHCl_3$/MeOH (1:1 ratio) the lower phases were dried down, resuspended in 50 μl of $CHCl_3$/MeOH (2:1 ratio) and analyzed by TLC. Cn 5607 specifically cleaves SGs, thus Cn 5607 was renamed as Sterylglucosidase1 (Sgl1).

The pH dependence of Sgl1 was determined using as substrate SGs in a pH range of 4.5-8 using the following buffers at the final concentration of 50 mM: sodium acetate (pH 4.5-5.0), MES (pH 5.5-6.0), sodium phosphate (pH 6.5-7.0), and HEPES (pH 7.5-8.0). The optimal temperature of Sgl1 was determined in the range from 25 to 37° C. The effect of detergents was assessed using Triton X-100, Sodium Deoxycholate and CHAPS at the concentration of 0.05, 0.15, and 0.3%.

In Vitro Activity Assay of Cn 5607 Using NBD-$C_6$-Glucosylceramide and Cn Lone Chain GlcCer To verify the enzymatic activity of Cn 5607, different substrates were used: NBD-$C_6$-glucosylceramide (NBD-$C_6$-GlcCer; Matreya, LLC, State-College, Pa., USA) and Cn long chain GlcCer. Briefly, 200 µg of yeast proteins from ScΔYIR+empty vector or ScΔYIR-Cn 5607 were incubated first with 20 µM of NBD-$C_6$-Glucosylceramide and at 30° C. for 1 h in a final reaction volume of 100 µl. The production of NBD-$C_6$-Ceramide was identified as a fluorescent band using a PhosphorImager™ 860 STORM unit and ImageQuant analysis (GE Healthcare, Rahway, N.J., USA) as previously described (Rittershaus et al., 2006).

The in vitro Cn 5607 activity was also valuated using 10 µg of Cn long chain GlcCer and 200 µg of ScΔYIR+empty vector or ScΔYIR-Cn 5607 cell extracts. Cerezyme (10 µg), generously provided by the Genzyme Corporation (Cambridge, Mass., USA), was used as positive control for the catalytic reaction. The reactions were terminated by the addition of 300 µl of $CHCl_3$/MeOH (1:1 ratio), the samples were mixed and the phases were separated by centrifugation at 3000 g for 5 min. The lower phases were dried down using a SPD 2010 SpeedVac vacuum dryer (Thermo Electron Corp.). The dried samples were resuspended in 50 µl of $CHCl_3$/MeOH (2:1 ratio) and analyzed by TLC on silica gel plate (EMD Millipore, Billerica, Mass., USA) developed with chloroform/methanol/water (65:25:4, v/v/v) and stained with iodine and resorcinol. The in vitro activity assay using Cn long chain GlcCer and ScΔYIR+empty vector or ScΔYIR-Cn 5607 was also repeated with a longer incubation time (4 h) and the results were evaluated by liquid chromatography-mass spectrometry (LC-MS).

Disruption and Reconstitution of SGL1 Gene in Cn

Figure 7A:
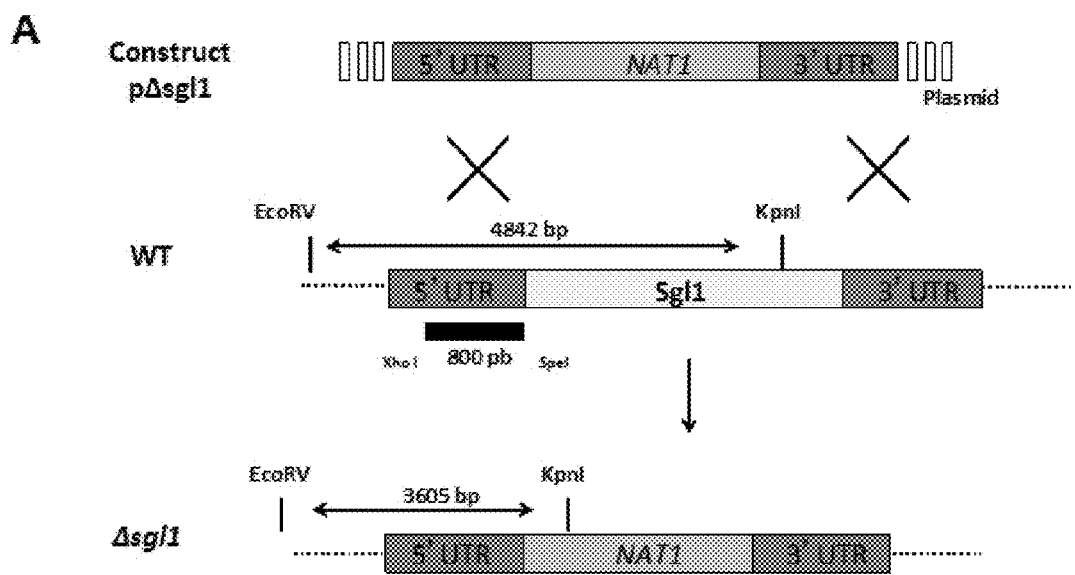
Figure 7B:
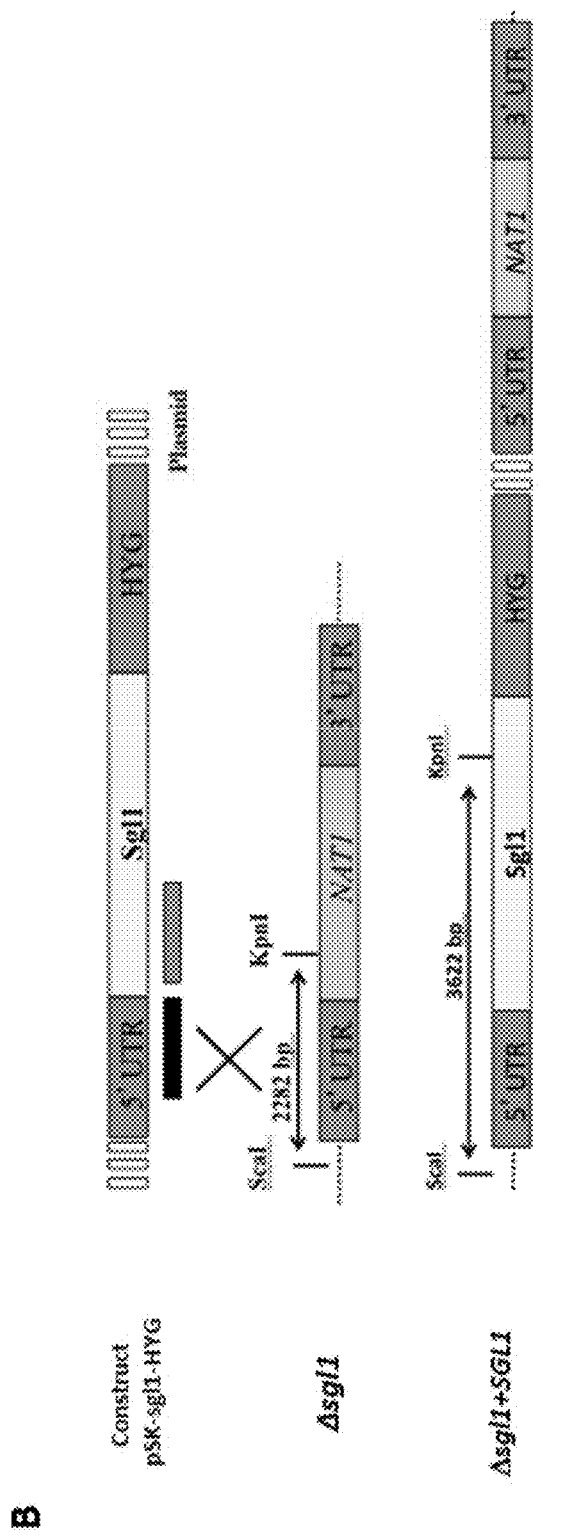

The SGL1 gene (locus number CNAG_05607 in *C. neoformans* var. *grubii* serotype A genome database) was deleted using NAT1 (Nourseothricin Acetyl transferase1) split marker. A knockout cassette was generated containing a 1.035 bp of the 5' untranslated region (5'UTR) upstream of the ATG start codon of the SGL1 gene and a 1.059 bp of the 3'UTR. The 5'UTR was amplified by PCR using H99 genomic DNA as a template and the following primers: 5'UTR-F (5'-GTCAAGCTAA GAGCTCCATTTGATCAGCGGGATTCT-3') (SEQ ID NO: 3) and 5'UTR-R (5'-TCCACTCCGA ACTAGTATCGCGTAAACGAAGAGGTG-3') (SEQ ID NO: 4), containing SacI and SpeI sites, respectively (underlined). The 3'UTR was amplified by PCR using H99 genomic DNA as a template and the following primers: 3'UTR-F (5'-GTCAAGCTAATCTAGAAGCCCATTCTG-GTTGTTCTG-3') (SEQ ID NO: 5) and 3'UTR-R (5'-ACAT-CACACTTCTAGATTTAGCGAGCCACGTTTCT-3') (SEQ ID NO: 6). The amplified fragments were cloned in pCR II-TOPO and sequenced, generating plasmid pCR-5'UTR-TOPO and pCR-3'UTR-TOPO. NAT1 gene, which confers resistance to the antibiotic nourseothricin (Werner BioAgents, Jena, Germany), under the control of Cn actin promoter was digested from the plasmid pCR-NAT1-TOPO by SacI and SpeI and ligated with 5'UTR digested with the same restriction enzyme generating pCR-5'UTR-NAT1-TOPO. Finally, pCR-5'UTR-NAT-TOPO was digested by EcoRV and ligated with 3'UTR generating the disruption cassette pCR-5'UTR-NAT1-3'UTR-TOPO that was named pΔsgl1. The deletion scheme is illustrated in FIG. 7A. Cn WT was transformed with the plasmid pΔsgl1 using biolistic DNA delivery device, as described previously (Toffaletti et al., 1993). Stable transformants were grown on YPD plates containing 100 µg/ml of nourseothricin. Colonies were chosen randomly and genomic DNA was isolated and digested with EcoRV and KpnI for Southern blot analysis. The DNA fragments were screened by probing with a fragment of 5'UTR. Transformant #106 showing deletion of the SGL1 gene by insertion of the NAT1 was chosen and designated Δsgl1 mutant strain. SGL1 gene was reintroduced back into the Δsgl1 using the reconstitution cassette pSK-SGL1-HYG, which had the Hygromycin B allele as selectable marker. The reconstitution scheme is illustrated in FIG. 7B. The plasmid pSK-SGL1-HYG was biolistically delivered into Δsgl1. Homologous recombinants were screened by Southern hybridization using a 800 bp fragment of the SGL1 open reading frame as probes. Transformant #21 showing reconstitution of SGL1 gene was designated Δsgl1+SGL1 reconstituted strain.

Wild-type, mutant, and reconstituted strains were characterized for their growth profile, capsule formation, stress response, and intracellular growth. For growth profile studies, WT, Δsgl1, and Δsgl1+SGL1 reconstituted strains were grown overnight in YPD at 30° C., the cells were washed three times with PBS, counted, and diluted to a final density of $10^4$ cells/ml in DMEM at pH 7.4 or pH 4 and incubated at 37° C. in the presence of 5% $CO_2$. Aliquots were taken at different time points, diluted, and plated in duplicates onto YPD agar plates for assessment of CFUs. Capsule thickness and melanin production were determined as previously described (Wang et al., 1995; Shea et al., 2006). For oxidative stress studies, strains were spotted in serial dilution (10, $10^6$, $10^5$, $10^4$, $10^3$) on YPD agar plates with 25 mM HEPES (pH 7 or pH 4) supplemented with 5 mM $H_2O_2$, cells growth was assessed after incubation at 30° C. for 96 h. Nitrosative stress response was studied by spotting the strains in serial dilution ($10^7$, $10^6$, $10^5$, $10^4$, $10^3$) on YNB agar plates with 25 mM succinate acid (pH 4) supplemented with 0.1 mM $NaNO_2$. Cell growth was assessed after 96 h of incubation at 30, 37° C. in atmospheric environment or 37° C. in the presence of 5% $CO_2$.

Phagocytosis and intracellular killing studies were performed in J774.16 macrophage-like cells as previously described (Tripathi et al., 2012). Briefly, for phagocytosis experiments cells were plated in a 96 well plate in Dulbecco's minimal essential medium (DMEM) supplemented with 10% fetal bovine serum (FBS). *C. neoformans* cells were grown overnight in YPD at 30° C. Cells were washed twice in PBS and counted. Approximately $10^5$ cells in DMEM+FBS medium were opsonized with 10 µg/ml of anti-GXM monoclonal antibody 18B7 (kindly provided by Dr. Arturo Casadevall) and added to macrophage-like cells activated with 50 units/ml of recombinant murine gamma interferon and 0.3 µg/ml of lipopolysaccharide at an effector-to-target ratio of 1:1. After incubation for 2 h, extracellular *C. neoformans* cells were washed with three changes of warm DMEM medium and fresh medium. Then, 200 µl of sterile water was added to each well and the macrophage-like cells were lysed by pipetting several times. CFUs were analyzed by plating them on YPD agar plates and the numbers of internalized fungal cells were reported. Intracellular killing were performed in the same way with the following change: extracellular *C. neoformans* cells were washed off once 2 h after the initial incubation and another time after 24 h of incubation. Macrophage-like cells were lysed after 24 h by pipetting several times and CFUs were analyzed by plating them on YPD agar plates.

Lipid Analysis of *Cryptococcus* Strains by TLC

Total lipids from *Cryptococcus* strains were extracted, as described previously (Singh et al., 2012). Briefly, a single colony of *Cryptococcus* strains was grown in 15 ml of YPD broth at 30° C. for 20 h at 250 rpm. *Cryptococcus* cells ($5\times10^8$) were placed in a single glass tube to which the Mandala extraction buffer was added (Mandala et al., 1995). Lipid extraction was performed according to the methods of Bligh and Dyer (Bligh and Dyer, 1959) followed by base hydrolysis. One set of dried samples was resuspended in 50 µl of $CHCl_3$/MeOH (2:1 ratio) and analyzed by TLC developed with chloroform/methanol/water (65:25:4, v/v/v) and stained with iodine and resorcinol, the other set was used for gas chromatography-mass spectrometry (GC-MS).

Lipid Profiling by Mass Spectrometry

Total lipids were extracted from *Cryptococcus* strains, using the methods described previously (Singh et al., 2012). For sterylglucosides analyses, extracted lipid samples were derivatized using N, O-bis (trimethylsilyl) trifluoroacetamide/trimethylchlorosilane reagent (Sigma-Aldrich) and then analyzed using 30 mt (0.25 µm) DB5-MS column on Agilent 7890 GC-MS (Agilent Technologies, Santa Clara, Calif., USA). The retention time and mass spectral patterns of plant SGs standard (Avanti Polar Lipids, Inc., Alabaster, Ala., USA) were used as a reference (Gutierrez and del Rio, 2001). Cholesterol was added as an internal standard for these analyses prior to lipid extraction. Ceramide and glucosylceramide species were analyzed by multiple reactions monitoring (MRM) as described previously (Singh et al., 2012) using TSQ Quantum Ultra™ Triple Quadrupole Mass Spectrometer (Thermo Scientific, USA). Samples were delivered by Accela pump (Thermo Finnigan, USA) to the HPLC fitted with 3 µm C8SR, 150 mm×3.0 mm column (Peeke Scientific, Sommerset, N.J., USA). C17 sphingosine and C17 ceramide were added as an internal standard for these analyses prior to lipid extraction. Determination of plant sterols and sterylglucosides for enzymatic activity assay was performed using MRM monitoring on LC-MS (Wewer et al., 2011). Standard plant sterols and sterylglucosides (Avanti Polar Lipids, Inc.) were used as the external standards in these measurements.

Animal Studies

Four weeks old female CBA/J mice (Harlan Laboratories, Indianapolis, Ind., USA) were used for all studies. Mice were anesthetized with an intraperitoneal injection of 60 µl xylazine/ketamine mixture containing 95 mg ketamine and 5 mg xylazine per kilogram of body weight and infected. For the infection studies, 24 mice (eight for each group) were infected intranasally with $5\times10^5$ cells/20 µl of WT, $\Delta$sgl1 or $\Delta$sgl1+SGL1 reconstituted strain. Mice were inspected twice a day and those that appeared moribund or in pain were sacrificed with $CO_2$ inhalation followed by cervical dislocation. All animal procedures were approved by Stony Brook University Institutional Animal Care and Use Committee and followed the guidelines of American Veterinary Medical Association. For tissue burden analysis, four mice per strain were used. Lung, brain, liver, kidney and spleen were excised and homogenized in 10 ml of PBS using Stomacher 80 (Seward, UK) for 2 min at high speed. Several dilutions were plated in duplicate onto YPD agar plates and incubated for 48-72 h at 30° C. The CFUs per organ were counted. For histopathology analysis, three mice per strain were used. Mice organs were fixed in 3.7% of formaldehyde in paraffin and stained with haematoxylin and eosin and mucicarmine.

For in vivo vaccination studies, mice were pre-treated with vehicle (PBS), $\Delta$sgl1 ($5\times10^5$ cells), and $\Delta$gcs1 ($5\times10^5$ cells). After 30 days, mice pre-treated with vehicle or $\Delta$sgl1 were challenged with $5\times10^5$ cells of Cn WT or Cg R265. Mice pre-treated with $\Delta$gcs1 were challenged with $5\times10^5$ cells of Cn WT. Mouse survival was monitored for 80 days after post-challenge. $CD4^+$ T-cell depletion was achieved by weekly intraperitoneal administration of anti-$CD4^+$ (GK1.5, rat IgG2b, 200 µg in 200 µL of PBS; National Cell Culture Center, Minneapolis, Minn., USA). A rat IgG2b (eBioscience, Inc., San Diego, Calif., USA) was used as control. T-cell depletion was assessed by flow cytometry in the spleens. For vaccination studies, mice (eight for each group) were pre-treated with vehicle (PBS) or $\Delta$sgl1 strain after 48 h from the first round of T-cell depletion and after 30 days were challenged with a lethal dose of Cn WT ($5\times10^5$ cells) and their survival was monitored for 80 days.

Example 1

CNAG_05607 has Sterylglucosidase and not Glucosylceramidase Activity

Figure 5:
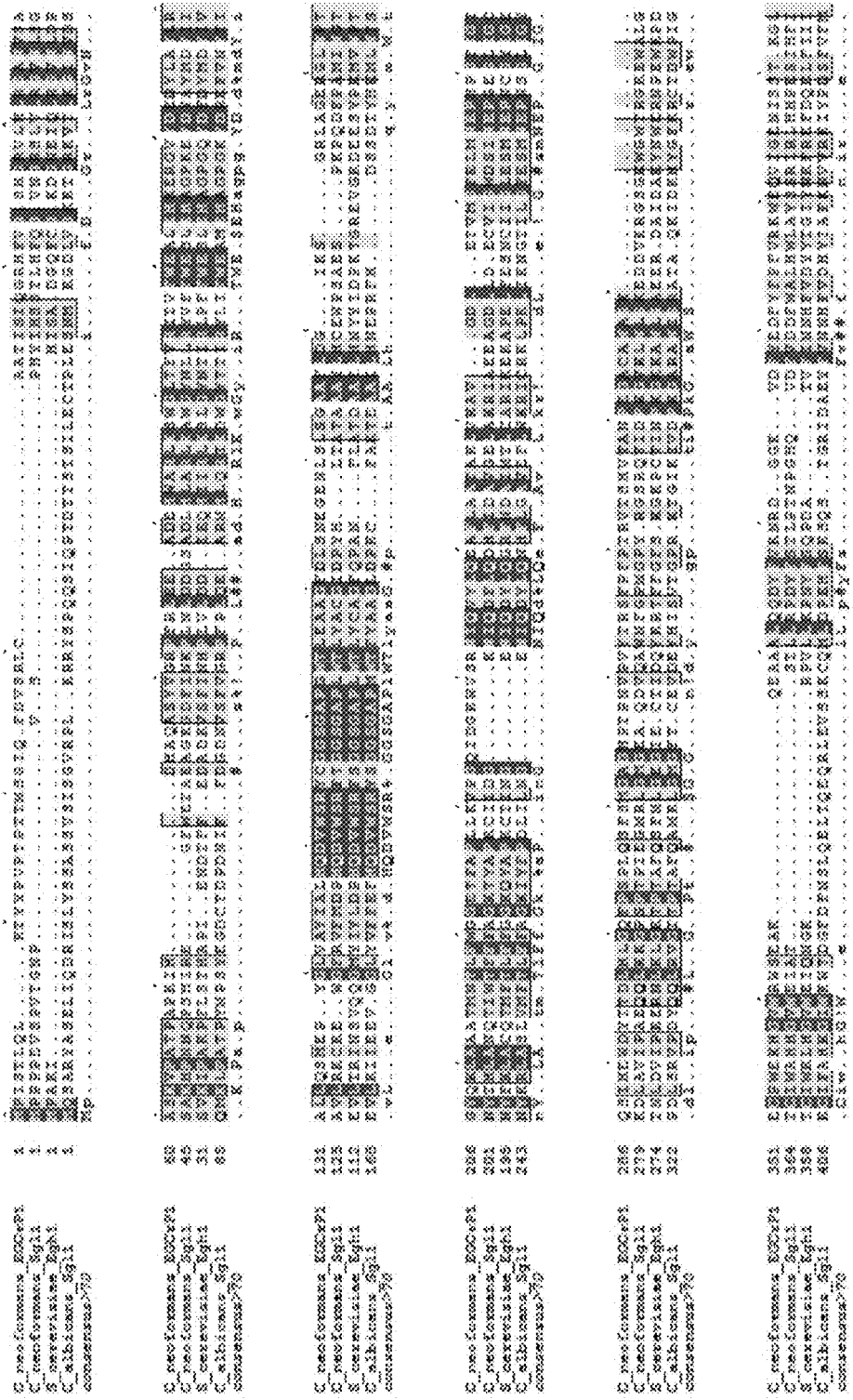
Figure 6:
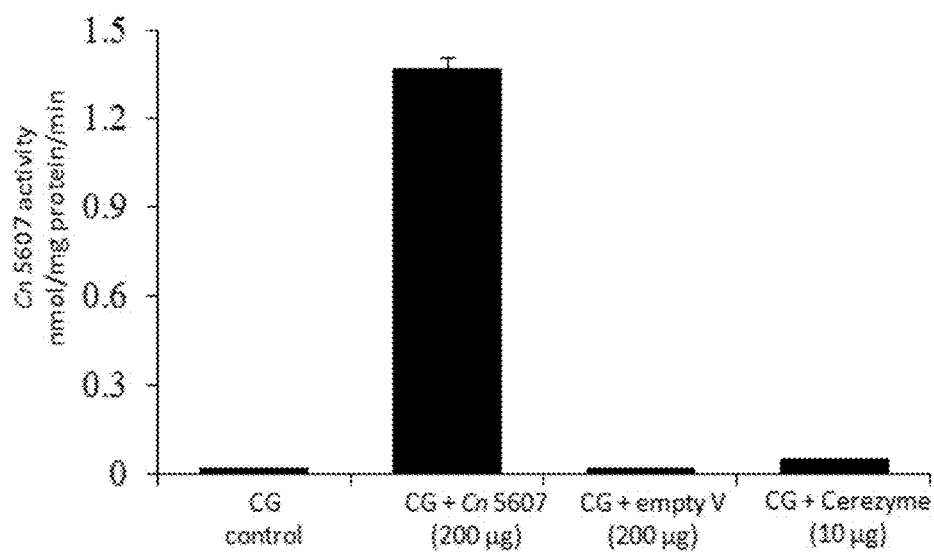

An *S. cerevisiae* expression system was used for characterizing the activity of the CNAG_05607 enzyme. The blast search of CNAG_05607 in *Saccharomyces* genome database revealed a gene YIR007W with an identity of 41% (expect=1.8e-129) to CNAG_05607 (FIG. 5). Therefore, a Sc$\Delta$YIR mutant strain lacking of YIR007W gene was used for the studies. CNAG_05607 was cloned in pYES/CT vector and overexpressed in *S. cerevisiae* YIR007W mutant strain (Sc$\Delta$YIR+Cn 5607). As a negative control, Sc$\Delta$YIR mutant was transformed with pYES/CT empty vector (Sc$\Delta$YIR+empty vector). Total proteins were extracted from *S. cerevisiae* strains, which contained the empty vector (control) or overexpressed the CNAG_05607 enzyme, and were incubated with plant (FIG. 1A) or cryptococcal sterylglucosides (SGs; FIG. 1B). With either substrate, 100 µg of total protein extract was enough to significantly degrade the SGs as evidenced by the disappearance of the SGs band on the TLC. No difference in the intensity of the SGs band was detected compared to the SG control when Sc$\Delta$YIR mutant strain carrying the empty vector was incubated with plant or cryptococcal SGs. The activity of the enzyme was dependent on pH (FIG. 1C) and temperature (data not shown), with the maximum activity observed at a pH 4.5 in sodium acetate buffer and a temperature of 37° C. In addition to cryptococcal SGs, the CNAG_05607 enzyme was also able to degrade cholesterol glucoside, the mammalian form of SGs (FIG. 6).

The CNAG_05607 enzyme has recently been characterized as a glucosylceramidase due to its ability to hydrolyze short-chain glucosylceramides (Watanabe et al., 2015). Our initial biochemical characterization also showed that CNAG_05607 metabolizes short chain glucosylceramide (data not shown) similarly to what was observed by Watanabe et al. (2015). However, CNAG_05607 did not metabolize long-chain, physiologically relevant, $\Delta$8-C9 methyl glucosylceramides (FIGS. 1D,E), which is the form of glucosylceramide found in *C. neoformans*. To the best of our knowledge, glucosylceramide synthase and glucosylcerebrosidase, do not need a co-factor or activator to exert their activity on long chain GlcCer (i.e., C16 GlcCer; Akiyama et al., 2013). Cerezyme, a human recombinant glucosylcerebrosidase, was used as control. This enzyme metabolized NBD-$C_6$-GlcCer (data not shown) as well as long-chain *Cryptococcus*$\Delta$8-C9 methyl glucosylceramides resulting in ceramide production (FIG. 1E). Cerezyme did not exhibit activity on plants or cryptococcal SGs (data not shown). Thus, these results demonstrate that CNAG_05607 has specific activity toward sterylglucosides, therefore this enzyme was re-named Sterylglucosidase 1 (Sgl1).

Example 2

Deletion of SGL1 Causes Accumulation of SGs and not GlcCer

Figures 2A, 2B, 2C, 2D, 2E, 2F, 2G:
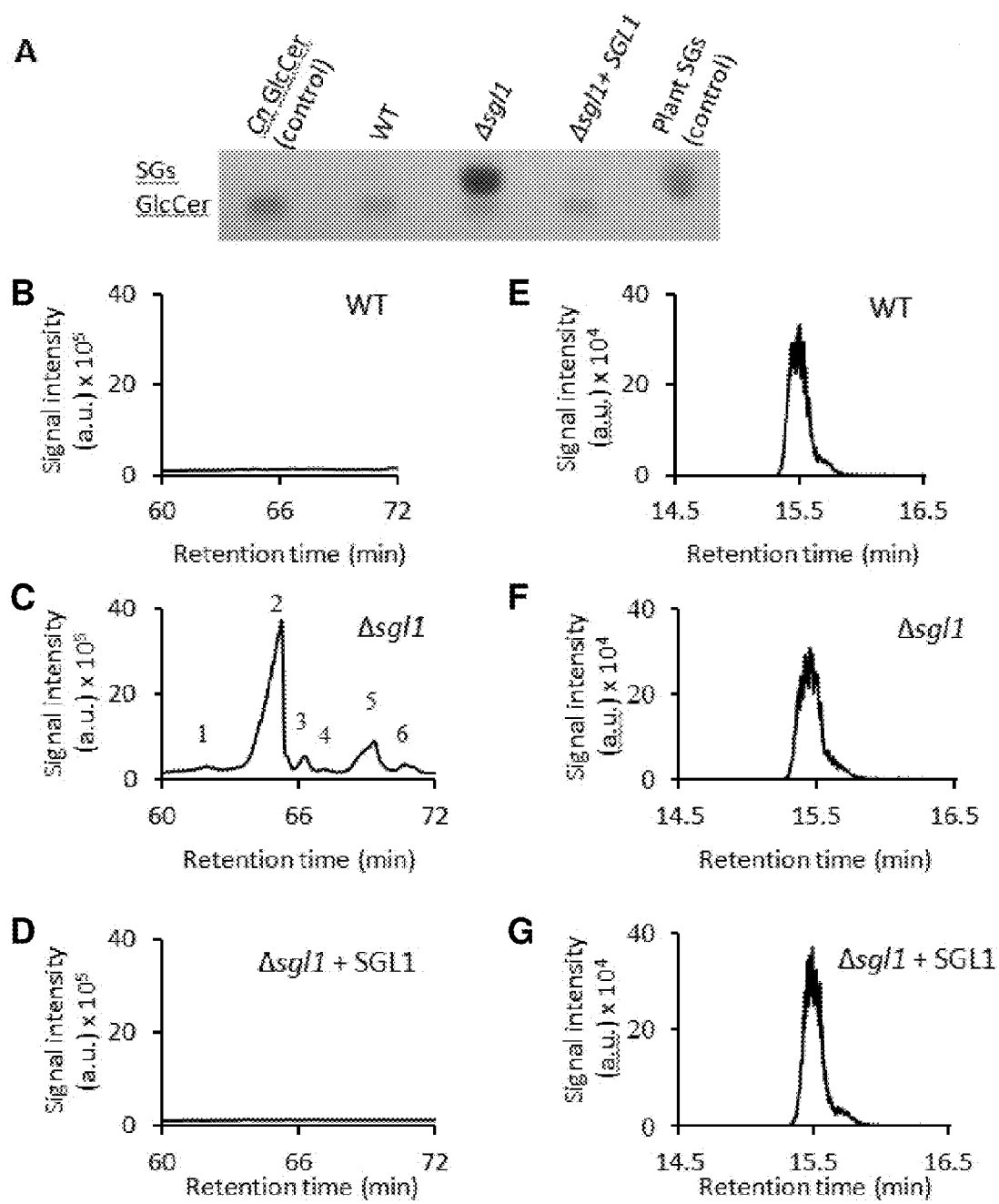
Figure 7C:
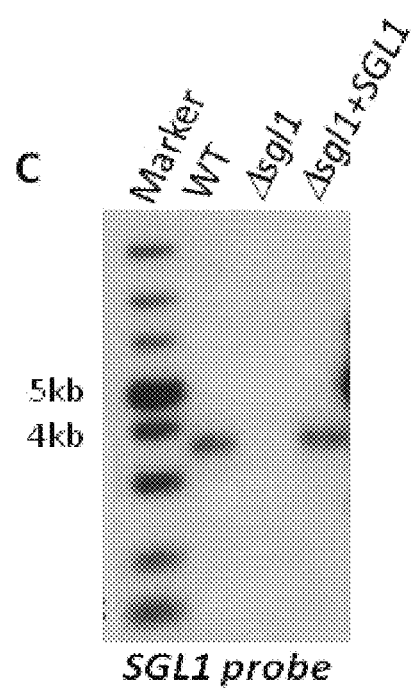
Figures 8A, 8B, 8C, 8D, 8E, 8F:
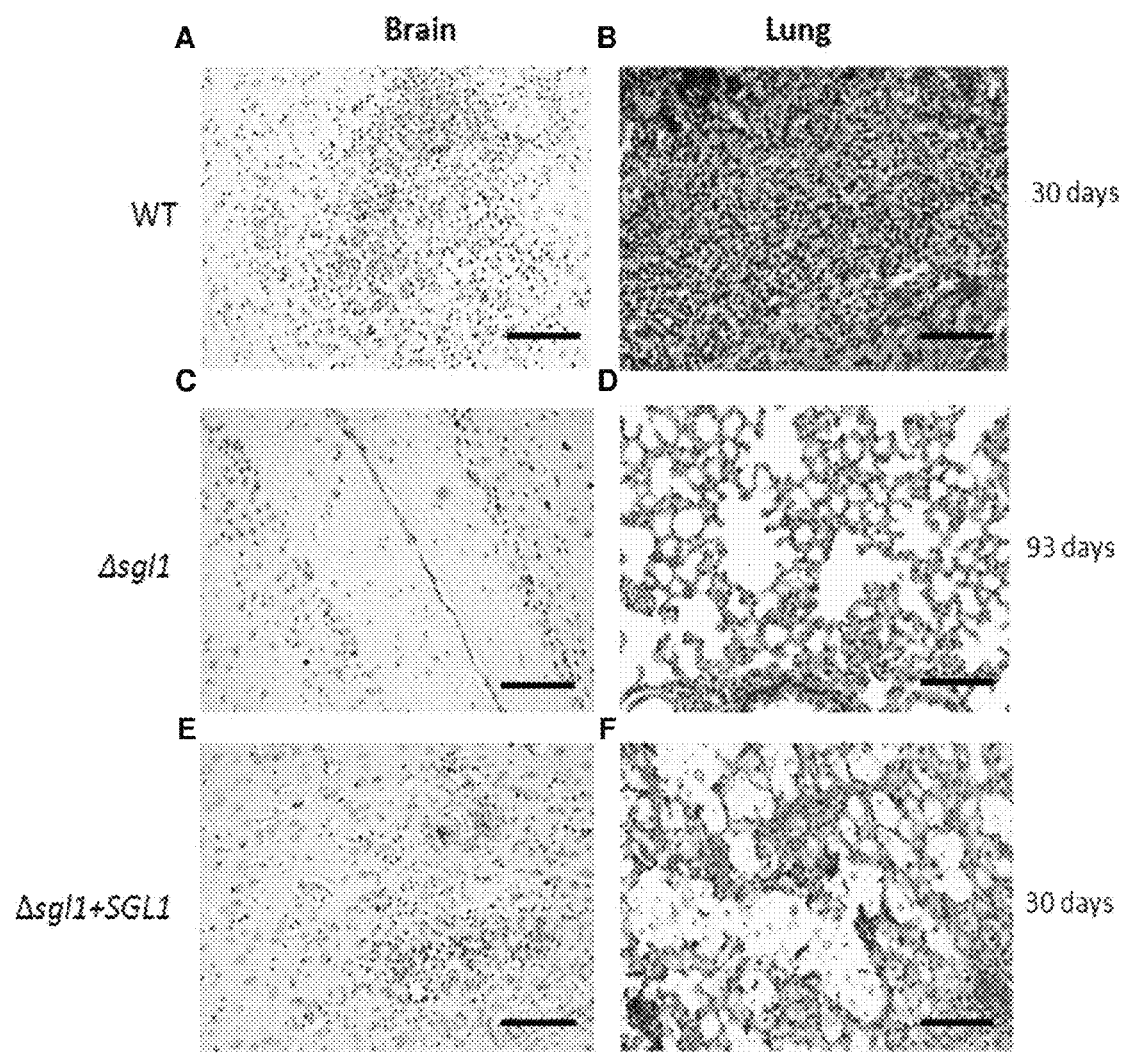

Since the Sgl1 enzyme acts to metabolize cryptococcal SGs, deletion of this enzyme in *C. neoformans* should lead to a SGs accumulating strain. This hypothesis was tested by genetically eliminating the sterylglucosidase enzyme (FIG. 7) in *C. neoformans* and monitoring the lipid profile by performing TLC and GC-MC on the total lipids extracted from the WT and the mutant strain. It was found that while the WT *C. neoformans* produces very little SGs, genetic elimination of sterylglucosidase (the Δsgl1 mutant) leads to a dramatic SGs accumulation; a phenomenon that is restored in the reconstituted strain (Δsgl1+SGL1; FIGS. 2A,B). In agreement with the in vitro activity studies, elimination of sterylglucosidase did not affect glucosylceramide levels in the cell (FIGS. 2E-2F), further confirming the sterylglucosides-specific activity of this enzyme.

Figure 2H:
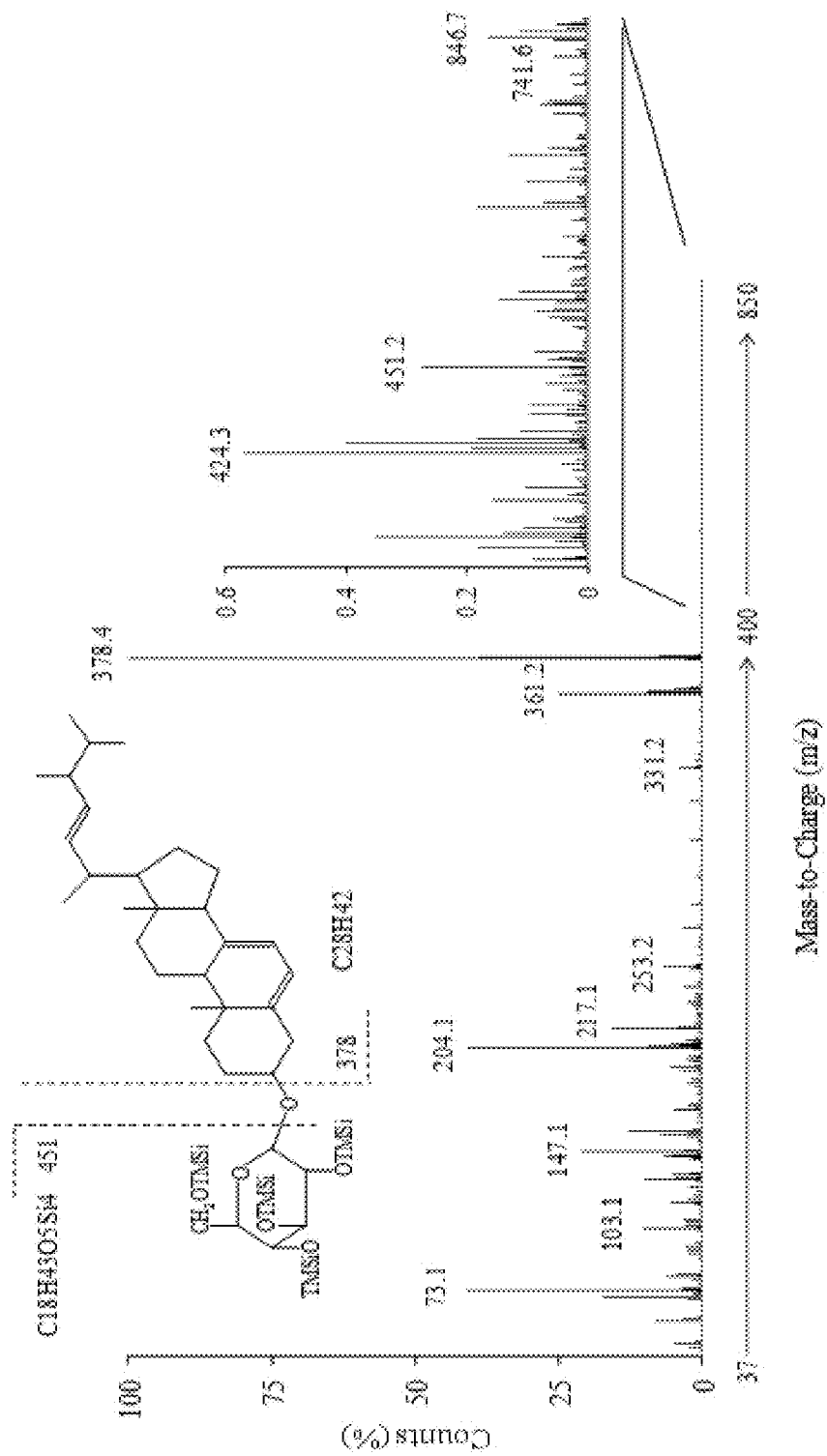

In depth analysis of the MS spectrum of Δsgl1 strain showed the accumulation of 9 structures (FIGS. 2B-2D) with ion fragments of m/z 147, 204, 217, 305, 361, 451. These structures were characteristic of tetramethylsilyl (TMSi) glucose ion fragments resulting from cleavage of C—O bonds. The fragments with m/z 361 and 451 are representative of TMSi derivative of hexoses. Ion fragments with m/z 129 and 255, characteristic of steroid moiety, were also present. Ion fragments with m/z of 73 and 147 represent the cleavage of 1 TMSi and 2 TMSsi groups respectively. The signal intensity of ion m/z 204 was greater than 217, which represented pyranoside configuration of the O-glycosidic linkage. These ion fragments resembled the fragmentation pattern generated during the MS analysis of plant sterylglucosides. Gutierrez and del Rio, 2001). Altogether, the ion fragments analysis confirmed that the structure possessed all characteristics of sterylglucosides. One of the most accumulated structures in the Δsgl1 mutant was ergosterolglucoside (Peak 2, FIG. 2C). Apart from other characteristic ion fragments of sterolglucoside, MS fragmentation of peak 2 showed an ion fragment of m/z 378, which results from the cleavage C—O linkage of O-linked glucose moiety and is characteristic to ergosterol, suggesting that ergosterolglucoside was the structure with the highest concentration in the Δsgl1 strain. The chemical structure and the electron-impact mass spectrum of this molecule is presented in FIG. 2H.

Example 3

Sgl1 is a Virulence Factor of *C. neoformans*

Figures 3A, 3B:
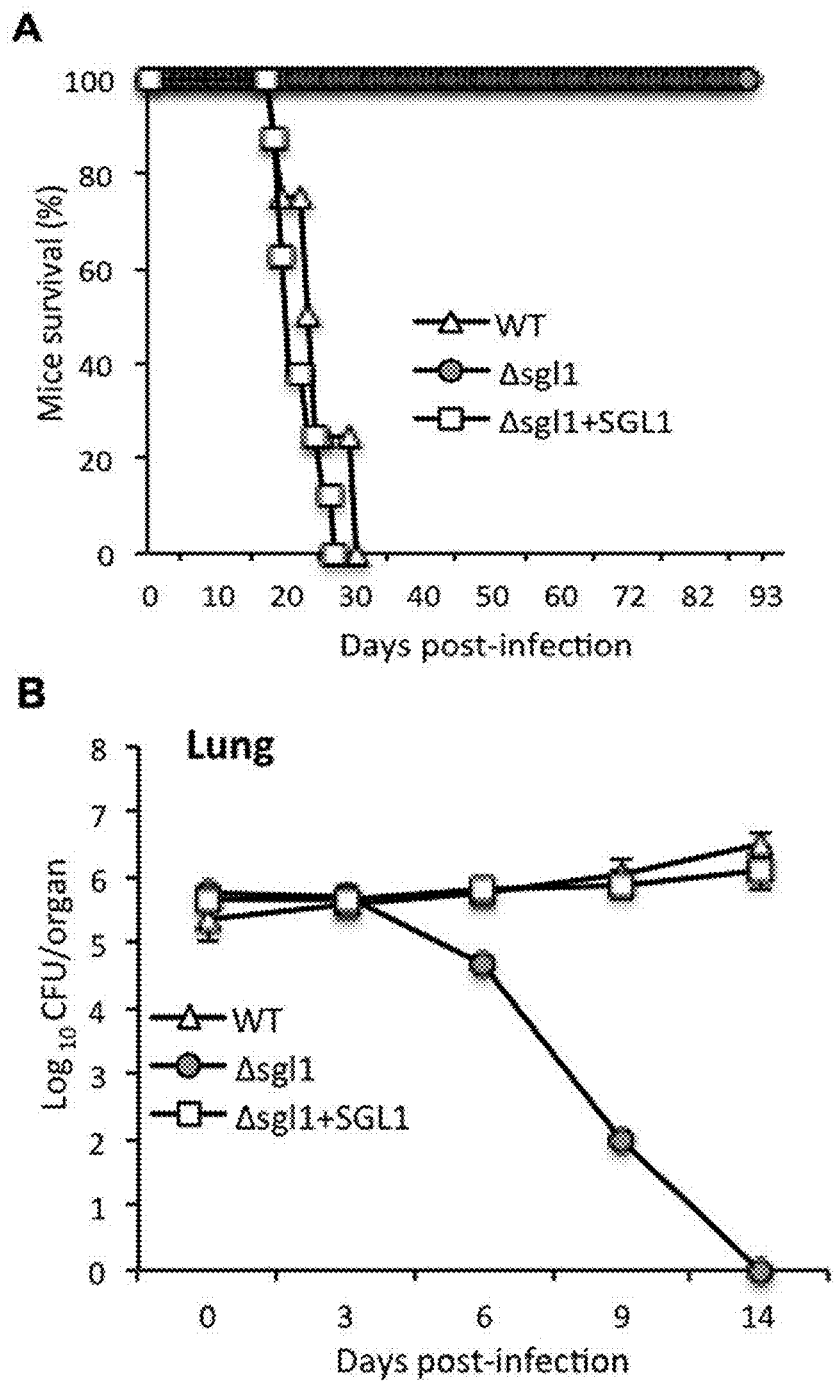

Alterations in sphingolipid metabolism have been shown to attenuate cryptococcal virulence (Rittershaus et al., 2006; Singh et al., 2012). Thus, the virulence of the Δsgl1 strain in the mouse model of cryptococcosis was tested. Mice were infected with a lethal dose of fungal cells ($5 \times 10^5$ cells) to establish cryptococcosis and monitored for their survival. The average survival of mice infected with the WT *C. neoformans* was 24±6 days whereas all mice infected with Δsgl1 strain remained alive during the course of the experiment (i.e., 90 days post-infection). Mice infected with the Δsgl1+SGL1 strain showed a survival pattern similar to that observed in the WT (average survival of 21±7 days; FIG. 3A). During the course of infection, lungs and brains were removed from the mice infected with the three strains and analysis of tissue burden was performed at days 0, 3, 6, 9, and 14 post-infection.

Figure 3C:
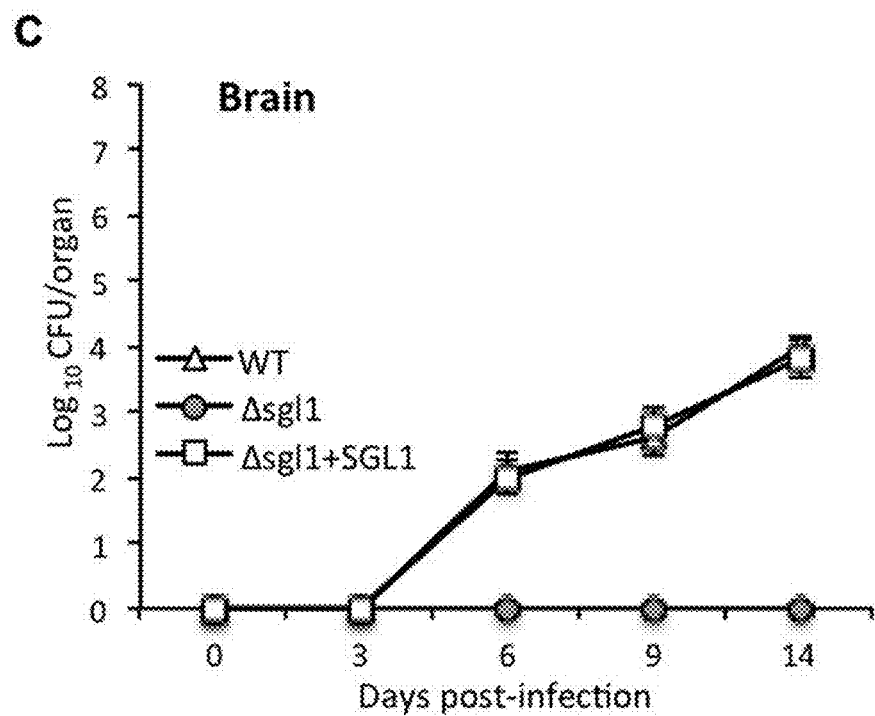

Interestingly, the number of Δsgl1 cells in the lungs decreased starting at day 3 and continued until day 14, at which point the lungs were completely clear of fungal cells (FIG. 3B). Furthermore, no Δsgl1 cells were observed in the brain (FIG. 3C), suggesting that fungal cells did not disseminate to the brain in the Δsgl1-infected mice. In contrast, a significant number of fungal cells were found in the lungs and brains of mice infected with the WT or the Δsgl1+SGL1 strain (FIGS. 3B, C). In both cases, the number of fungal cells in the brain increased as a function of time, demonstrating the occurrence of extrapulmonary dissemination and progression of the disease. The findings of the tissue burden studies were confirmed by lung and brain histology observations, which showed no fungal cells in the organs isolated from the Δsgl1-infected mice at the end of the experiment, but significant tissue damage and presence of fungal cells in the WT or Δsgl1+SGL1 strains (FIG. 8A-8F). These experiments reveal that sterylglucosidase is a virulence factor in *C. neoformans*, as the loss of this enzyme leads to loss of virulence in the mouse model.

Example 4

The ΔSgl1 Strain Acts as a Vaccine Against Cryptococcosis in the Mouse Model

Figures 9A, 9B, 9C, 9D, 9E, 9F:
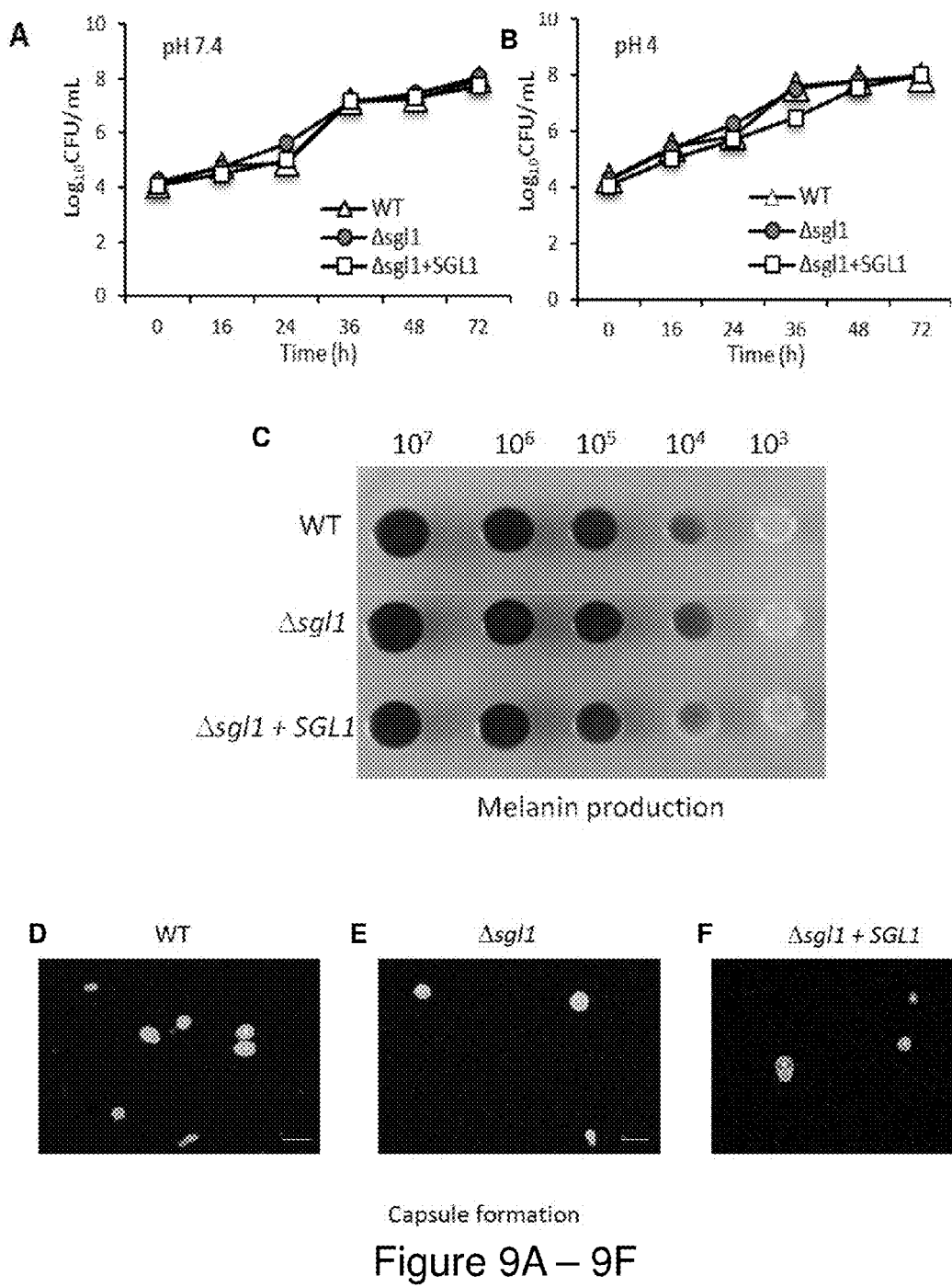
Figure 9G:
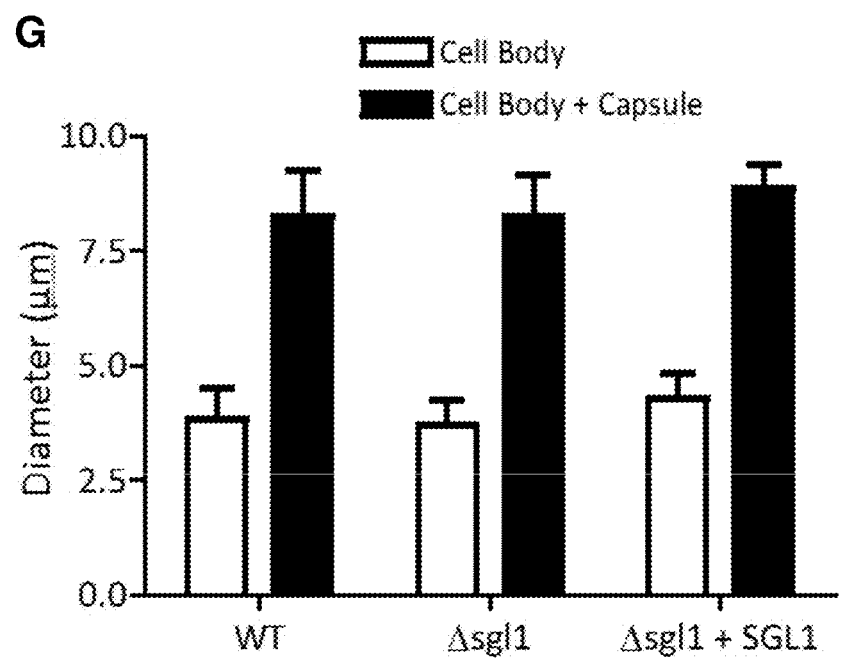
Figure 9H:
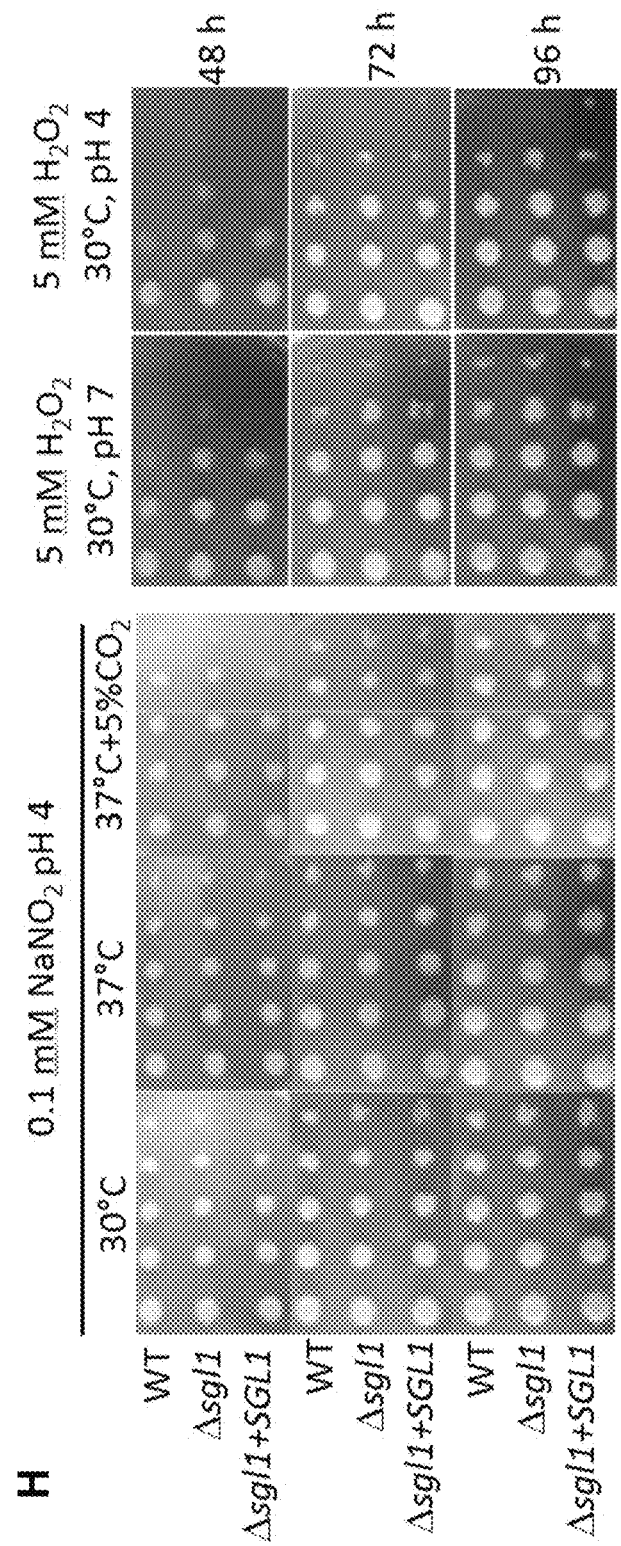
Figures 9I, 9J:
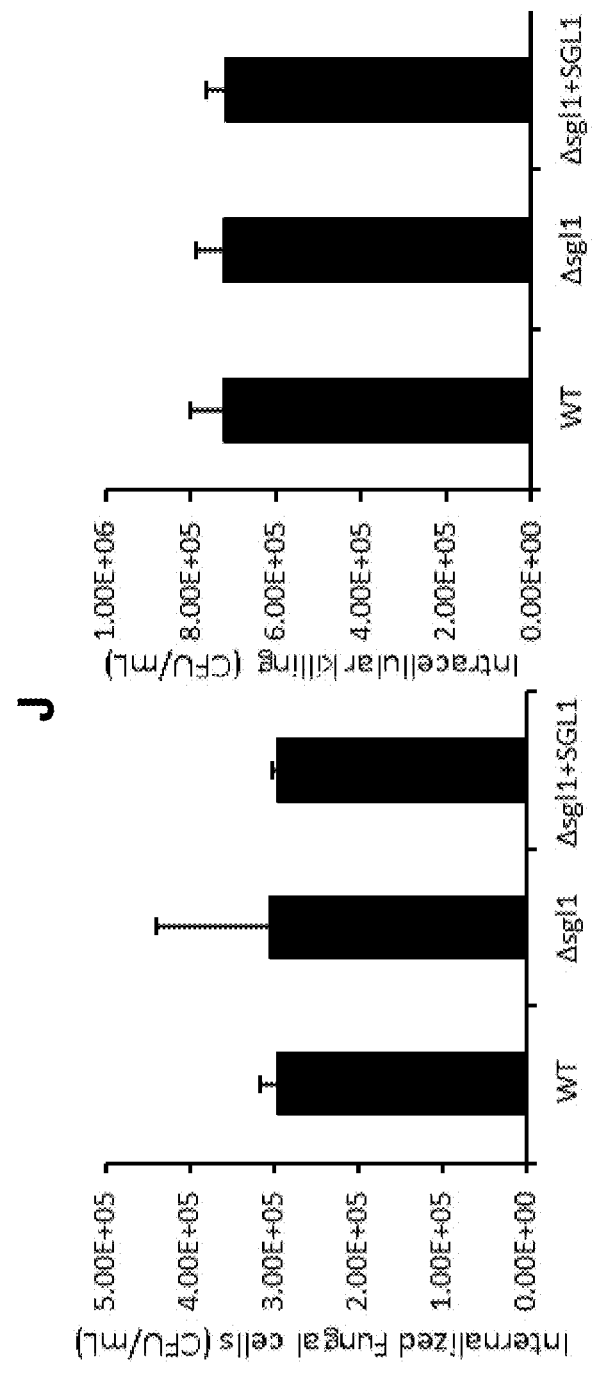

*Cryptococcus neoformans* cells possess a number of virulence factors that contribute to their survival inside the host, resistance to immune response, and detrimental activity against the host (Coelho et al., 2014). To gain more insight into the loss of virulence of the Δsgl1 strain, a number of virulence factors in this strain were evaluated and compared to the WT. In comparison to the WT, the Δsgl1 strain showed similar growth in acidic and neutral pH (at 37° C. and in the presence of 5% $CO_2$), similar melanin production and capsule thickness, and no major difference in growth under oxidative or nitrosative stress. In addition, the WT and mutant strains showed similar intracellular growth during in vitro infection of the J774.16 macrophage-like cells (FIG. 9A and FIG. 9B). These analyses suggest that the most common virulence factors are similar between the Δsgl1 strain and the WT denoting a different mechanism for the loss of virulence.

Figures 4A, 4B:
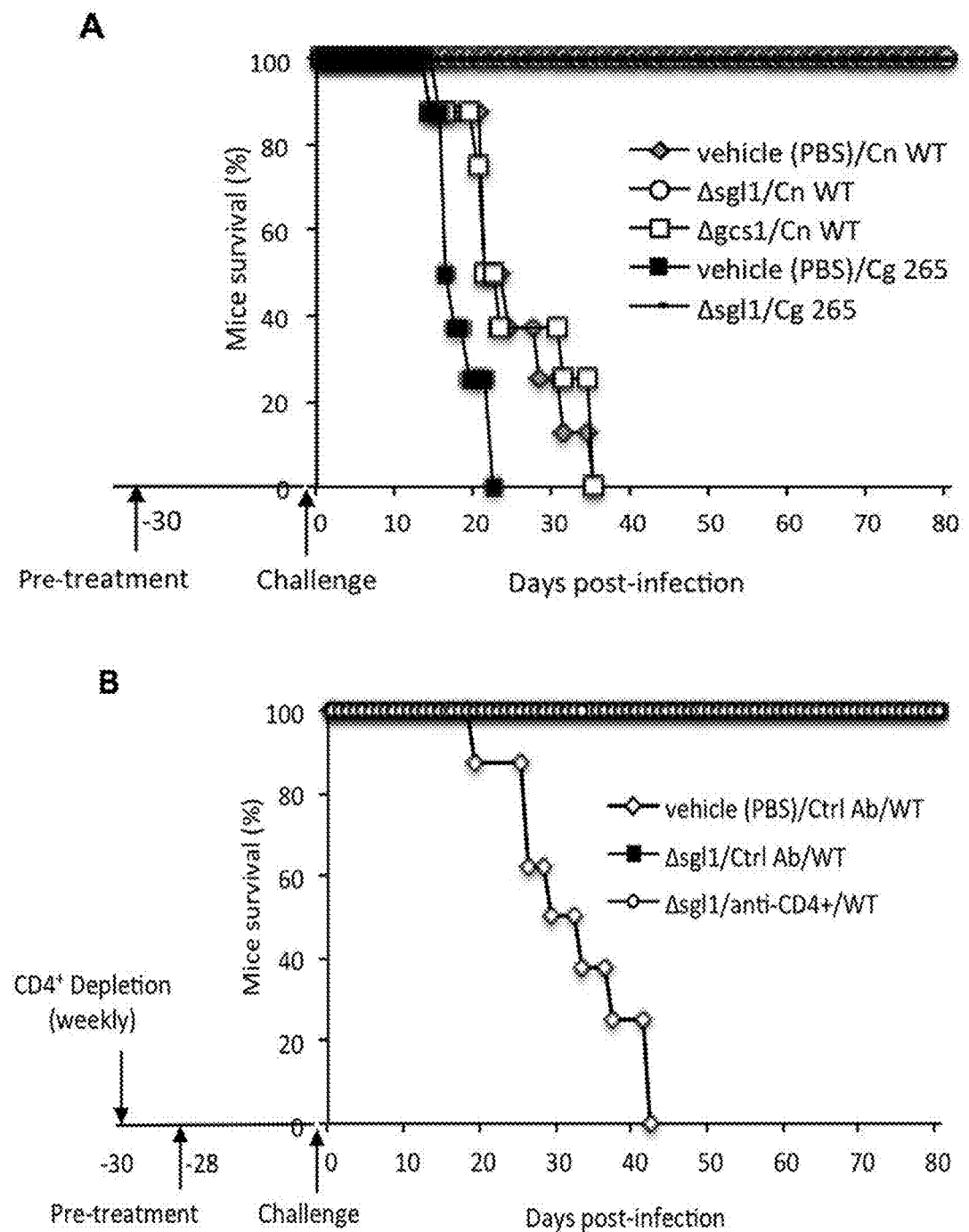

Given that the Δsgl1 strain was non-pathogenic and that SGs are known immunostimulators (Lee et al., 2007; Grille et al., 2010), the potential use of the Δsgl1 strain as a vaccine against cryptococcosis was investigated. Two controls were used for these studies: a vehicle (sterile PBS) and the *C. neoformans* Δgcs1 strain (Rittershaus et al., 2006), which is avirulent, but does not accumulate SGs. Mice were infected with the vehicle, or $5 \times 10^5$ cells of the Δgcs1 or the Δsgl1 strains and after 30 days were challenged with a lethal dose of the virulent WT *C. neoformans* or *C. gattii* R265 strains. Interestingly, the mice that were pre-treated with the Δsgl1 strain were completely protected against the subsequent infection. However, the mice that were pre-treated with the vehicle or the Δgcs1 strain succumbed to infection within 35 days (FIG. 4A). These results suggest that the Δsgl1 strain may stimulate a host immune response that successfully kills Δsgl1 and makes the host resistant to subsequent cryptococcosis.

Figures 4C, 4D:
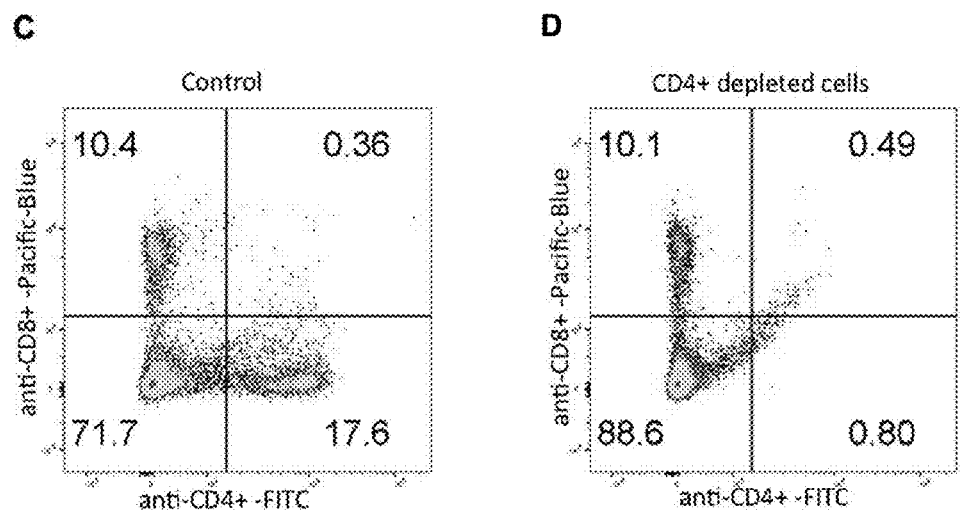

Although *Cryptococcus* infections can afflict immunocompetent individuals, the majority of the population at risk, are those suffering from immune suppression, such as HIV/AIDS patients. A reduction in $CD4^+$ T-cells in this population results in aggressive cryptococcosis, which can be life threatening (Jarvis et al., 2013). The efficiency of the $\Delta sgl1$ strain as a vaccine against cryptococcosis during immune suppression was examined by its administration in $CD4^+$ T-cells depleted mice prior to infection with the WT *C. neoformans*. For these studies, mice were depleted of $CD4^+$ by weekly administration of anti-$CD4^+$ antibody or control antibody (rat IgG2b) starting a month prior to infection with WT *C. neoformans* (FIG. 4B). A 94.3% percent reduction in $CD4^+$ T-cells was achieved as confirmed by flow cytometry (FIGS. 4C-4D). The $\Delta sgl1$ strain or control (PBS) was also administered to mice a month prior to infection. Mice were then infected with $5 \times 10^5$ cells of the virulent WT *C. neoformans*. All mice that received the PBS and the antibody control succumbed to infection in 41 days, while all the $CD4^+$ T-cells depleted mice that were vaccinated with the $\Delta sgl1$ strain survived the infection, demonstrating that this strain is not infectious and can protect immune suppressed mice against a subsequent cryptococcal infection (FIG. 4B).

Example 5

$\Delta Sgl1$ Strain can be Used to Produce Sterylglucosides

*Cryptococcus neoformans* (Cn) cells produce sterylglucosides (SGs); but, in wild type fungal cells the level of this lipid in Cn cells is almost undetectable. This suggests that under normal growing conditions, wild type *Cryptococcus neoformans* cells highly regulate and breakdown this lipid, and hence only very little amounts are accumulated.

It has been demonstrated herein by the present inventors that the Sgl1 gene in *Cryptococcus neoformans* produces an enzyme that breaks down sterylglucosides. Inactivation of the sgl1 gene (or its homologs in other fungal species) leads to a significant accumulation SGs in fungal cells. The present disclosure, therefore, comprises the use of mutant fungi comprising an inactivated Sterylglucosidase (Sgl1) gene homolog to produce SGs. The present disclosure also comprises methods of SG purification from said mutant fungi.

An example method (protocol) for SG purification is described below. This example method (protocol) is by no means limiting, and one skilled in the art would know how to modify and optimize the given protocol further, e.g., for scaling up or scaling down the purification.

Briefly, mutant fungal strains are grown in 1.5 liters of YPD medium at 37 C for 24 hours (exponential phase—cell concentration in this phase is $\sim 10^6$/ml). YPD medium comprises 2% Bacto peptone (Difco), 1% Bacto Yeast Extract (Difco), and 2% glucose. The grown fungal cells are counted and Mandala extraction is done on the entire culture of approximately $5 \times 10^9$ total cells. Mandala extraction is carried out as described in Mandala et al., (1995), *The Journal of Antibiotics* 48.5: 349-356, the entire contents of which is expressly incorporated herein by reference. Then, lipid extraction is achieved with a Bligh and Dyer extraction on the dried Mandala tubes. Bligh and Dyer extraction is performed as described in Bligh, E. G. and Dyer, W. J. *Can. J. Biochem. Physiol.*, 1959, 37:911-917, the entire contents of which is expressly incorporated herein by reference and the resulting sample is dried. All the dried Bligh and Dyer tubes are combined into one tube by dissolving in 4 mL of Chloroform:acetic acid (99:1). If this solution is turbid, the tube is centrifuged for 5 min at 1500 g and supernatant is used for the column. In the next step a Sep-Pak Cis cartridge column (Sep-Pak™, Waters Associates, Milford, Mass., U.S.A.), is washed with 90 mL chloroform. The sample from the previous step in 4 mL of Chloroform:acetic acid (99:1) is added to the wetted Sep-Pak column. Column is rinsed with another 6 mL of Chloroform:acetic acid (99:1). The column is washed with 60 mL of Chloroform:acetic acid (99:1). The column is eluted with 60 mL acetone and the flow through is collected in test tubes, which contain the sample. All sample in the test tubes from the previous step is dried in speedVac and combined in one tube, by resuspending the dried samples in acetone and adding them to other tubes. Next, base hydrolysis is performed on the samples in the tube as described in (Mandala et al., 1995). The sample is dried again upon the base hydrolysis step and later dissolved in 4 mL of Chloroform:acetic acid (99:1).

Figure 10:
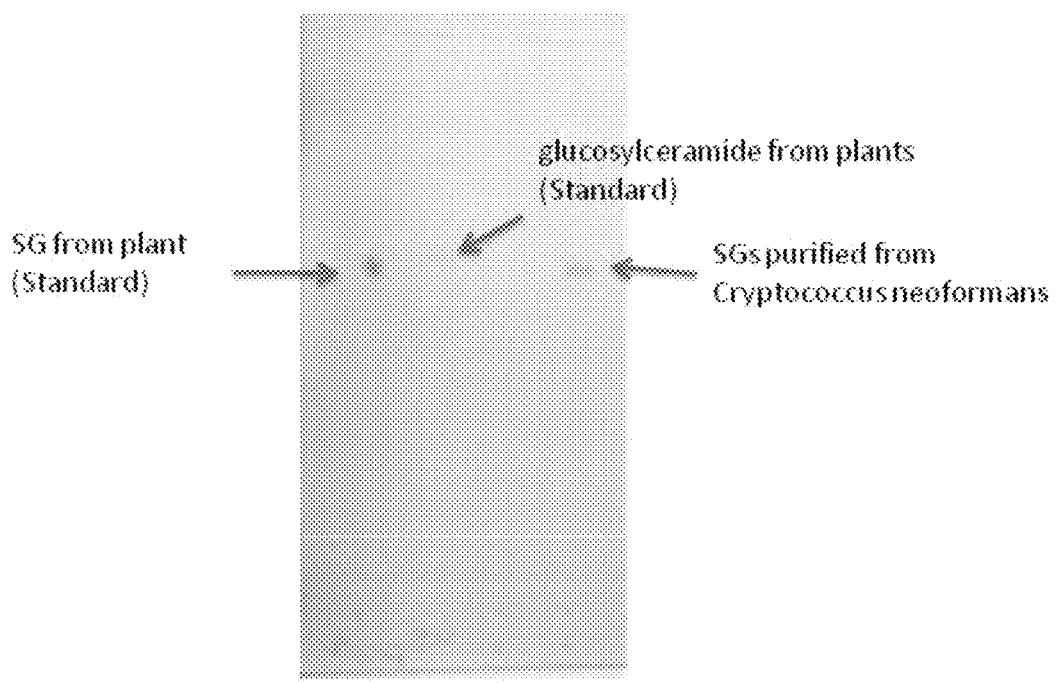

Following the first column purification, a second column purification is performed using a second Sep-Pak column. Briefly, the second column is first washed with 90 mL chloroform. Then the 4 mL of sample is added slowly to the second column. The sample tube is rinsed with 6 mL of chloroform:acetic acid (99:1) and added to the second column as well. The flow through is collected in tube 1. 20 mL of chloroform:acetic acid (99:1) is next added to the second column and collected in tube 2. 20 mL of chloroform:acetic acid (99:1) to the second column and collect in tube 3. Next, 14 mL of chloroform:acetic acid (99:1) is added to the second column and collected in tube 4, and when chloroform:acetic acid (99:1) has flown through, a 6 mL of chloroform:methanol (95:5) is added and collected in tube 4. 20 mL of chloroform:methanol (95:5) is added to the second column and collected in tube 5. 14 mL of chloroform:methanol (95:5) is added to the column and collected in tube 6, when chloroform:methanol (95:5) has flown through, then 6 mL of chloroform:methanol (90:10) is added and collected in tube 6. 20 mL of chloroform:methanol (90:10) is added to the second column and collected in tube 7. Another 20 mL of chloroform:methanol (90:10) is added to the column and collected in tube 8. Next, 14 mL of chloroform:methanol (90:10) is added to the column and collect in tube 9. Finally, 6 mL methanol is added to the second column and collected in tube 9. All tubes (1-9) are dried in the SpeedVac and then all lipids are dissolved in 1 mL of chloroform:methanol 2:1. For quality control 100 uL (10% of the overall sample) is dried it in SpeedVac, redisperses in 15 uL of Chloroform:methanol (2:1) and run on TLC (Thin layer Chromatography) plates to make sure that the purified lipid is found in tube 7. When running the TLC a plant sterolglycoside standard is run on the side of the sample in tube 6, to make sure that the SGs are properly purified. The TLC looks as shown in FIG. 10.

REFERENCES

Akiyama, H., Kobayashi, S., Hirabayashi, Y., and Murakami-Murofushi, K. (2013). Cholesterol glucosylation is catalyzed by transglucosylation reaction of beta-glucosidase 1. *Biochem. Biophys. Res. Commun.* 441, 838-843. doi: 10.1016/j.bbrc.2013.10.145

Bligh, E. G., and Dyer, W. J. A. (1959). rapid method of total lipid extraction and purification. *Can. J. Biochem. Physiol.* 37, 911-917. doi: 10.1139/o59-099

Bouic, P. J. (2001). The role of phytosterols and phytosterolins in immune modulation: a review of the past 10 years. *Curr. Opin. Clin. Nutr. Metab. Care* 4, 471-475.

Bouic, P. J., Etsebeth, S., Liebenberg, R. W., Albrecht, C. F., Pegel, K., and Van Jaarsveld, P. P. (1996). beta-Sitosterol and beta-sitosterol glucoside stimulate human peripheral blood lymphocyte proliferation: implications for their use as an immunomodulatory vitamin combination. *Int. J. Immunopharmacol.* 18, 693-700. doi: 10.1016/50192-0561(97)85551-8

Casadevall, A., Mukherjee, J., Devi, S. J., Schneerson, R., Robbins, J. B., and Scharff, M. D. (1992). Antibodies elicited by a *Cryptococcus neoformans*-tetanus toxoid conjugate vaccine have the same specificity as those elicited in infection. *J. Infect. Dis.* 165, 1086-1093. doi: 10.1093/infdis/165.6.1086

Casadevall, A., and Pirofski, L. (2005). Insights into mechanisms of antibody-mediated immunity from studies with *Cryptococcus neoformans*. *Curr. Mol. Med.* 5, 421-433. doi: 10.2174/1566524054022567

Chaturvedi, A. K., Hameed, R. S., Wozniak, K. L., Hole, C. R., Leopold Wager, C. M., Weintraub, S. T., et al. (2014). Vaccine-mediated immune responses to experimental pulmonary *Cryptococcus gattii* infection in mice. *PLoS ONE* 9:e104316. doi: 10.1371 l/journal.pone.0104316

Cheng, P. Y., Sham, A., and Kronstad, J. W. (2009). *Cryptococcus gattii* isolates from the British Columbia cryptococcosis outbreak induce less protective inflammation in a murine model of infection than *Cryptococcus neoformans*. *Infect. Immun.* 77, 4284-4294. doi: 10.1128/IAI.00628-09

Coelho, C., Bocca, A. L., and Casadevall, A. (2014). The tools for virulence of *Cryptococcus neoformans*. *Adv. Appl. Microbiol.* 87, 1-41. doi: 10.1016/B978-0-12-800261-2.00001-3

Datta, K., Bartlett, K. H., Baer, R., Byrnes, E., Galanis, E., Heitman, J., et al. (2009). Spread of *Cryptococcus gattii* into Pacific Northwest region of the United States. *Emerg. Infect. Dis.* 15, 1185-1191. doi: 10.3201/eid1508.081384

Datta, K., and Pirofski, L. A. (2006) Towards a vaccine for *Cryptococcus neoformans*: principles and caveats. *FEMS Yeast Res.* 6, 525-536. doi: 10.1111/j.1567-1364.2006.00073.x Decken, K., Kohler, G., Palmer-Lehmann, K., Wunderlin, A., Mattner, F., Magram, J., et al. (1998). Interleukin-12 is essential for a protective Th1 response in mice infected with *Cryptococcus neoformans*. *Infect. Immun.* 66, 4994-5000.

Devi, S. J. (1996). Preclinical efficacy of a glucuronoxylomannan-tetanus toxoid conjugate vaccine of *Cryptococcus neoformans* in a murine model. *Vaccine* 14, 841-844. doi: 10.1016/0264-410X(95)00256-Z Devi, S. J., Schneerson, R., Egan, W., Ulrich, T. J., Bryla, D., Robbins, J. B., et al. (1991). *Cryptococcus neoformans* serotype A glucuronoxylomannan-protein conjugate vaccines: synthesis, characterization, and immunogenicity. *Infect. Immun.* 59, 3700-3707.

Donald, P. R., Lamprecht, J. H., Freestone, M., Albrecht, C. F., Bouic, P. J., Kotze, D., et al. (1997). randomised placebo-controlled trial of the efficacy of beta-sitosterol and its glucoside as adjuvants in the treatment of pulmonary tuberculosis. *Int. J. Tuberc. Lung. Dis.* 1, 518-522.

Dong, Z. M., and Murphy, J. W. (1995) Effects of the two varieties of *Cryptococcus neoformans* cells and culture filtrate antigens on neutrophil locomotion. *Infect. Immun.* 63, 2632-2644.

Grille, S., Zaslawski, A., Thiele, S., and Plat, J. (2010). Warnecke D The functions of steryl glycosides come to those who wait: recent advances in plants, fungi, bacteria and animals. *Prog. Lipid Res.* 49, 262-288. doi: 10.1016/j.plipres.2010.02.001

Gutierrez, A., and del Rio, J. C. (2001). Gas chromatography/mass spectrometry demonstration of steryl glycosides in eucalypt wood, Kraft pulp and process liquids. *Rapid Commun. Mass Spectrom.* 15, 2515-2520. doi: 10.1002/rcm.537

Jarvis, J. N., Casazza, J. P., Stone, H. H., Meintjes, G., Lawn, S. D., Levitz, S. M., et al. (2013). The phenotype of the *Cryptococcus*-specific $CD^{4+}$ memory T-cell response is associated with disease severity and outcome in HIV-associated cryptococcal meningitis. *J. Infect. Dis.* 207, 1817-1828. doi: 10.1093/infdis/jit099

Kawai, S., Hashimoto, W., and Murata, K. (2010). Transformation of *Saccharomyces cerevisiae* and other fungi: methods and possible underlying mechanism. *Bioeng Bugs* 1, 395-403. doi: 10.4161/bbug.1.6.13257

Koguchi, Y., and Kawakami, K. (2002). Cryptococcal infection and Th1-Th2 cytokine balance. *Int. Rev. Immunol.* 21, 423-438. doi: 10.1080/08830180213274

Lee, J. H., and Han, Y. (2006). Ginsenoside Rg1 helps mice resist to disseminated candidiasis by Th1 type differentiation of $CD^{4+}$ T cell. *Int. Immunopharmacol.* 6, 1424-1430. doi: 10.1016/j.intimp.2006.04.009

Lee, J. H., Lee, J. Y., Park, J. H., Jung, H. S., Kim, J. S., Kang, S. S., et al. (2007). Immunoregulatory activity by daucosterol, a beta-sitosterol glycoside, induces protective Th1 immune response against disseminated Candidiasis in mice. *Vaccine* 25, 3834-3840. doi: 10.1016/j.vaccine.2007.01.108

Mandala, S. M., Thornton, R. A., Frommer, B. R., Curotto, J. E., Rozdilsky, W., Kurtz, M. B., et al. (1995). The discovery of australifungin, a novel inhibitor of sphinganine N-acyltransferase from *Sporormiella australis*. Producing organism, fermentation, isolation, and biological activity. *J. Antibiot.* (*Tokyo*) 48, 349-356. doi: 10.7164/antibiotics.48.349

Nanjappa, S. G., and Klein, B. S. (2014). Vaccine immunity against fungal infections. *Curr. Opin. Immunol.* 28, 27-33. doi: 10.1016/j.coi.2014.01.014

Park, B. J., Wannemuehler, K. A., Marston, B. J., Govender, N., Pappas, P. G., and Chiller, T. M. (2009). Estimation of the current global burden of cryptococcal meningitis among persons living with HIV/AIDS. *AIDS* 23, 525-530. doi: 10.1097/QAD.0b013e328322ffac Rittershaus, P. C., Kechichian, T. B., Allegood, J. C., Merrill, A. H. Jr., Hennig, M., Luberto, C., et al. (2006). Glucosylceramide synthase is an essential regulator of pathogenicity of *Cryptococcus neoformans*. *J. Clin. Invest.* 116, 1651-1659. doi: 10.1172/JCI27890

Shea, J. M., Kechichian, T. B., Luberto, C., and Del Poeta, M. (2006). The cryptococcal enzyme inositol phosphosphingolipid-phospholipase C confers resistance to the antifungal effects of macrophages and promotes fungal dissemination to the central nervous system. *Infect. Immun.* 74, 5977-5988. doi: 10.1128/IAI.00768-06

Singh, A., Qureshi, A., and Del Poeta, M. (2011). Quantitation of cellular components in *Cryptococcus neoformans* for system biology analysis. *Methods Mol. Biol.* 734, 317-333. doi: 10.1007/978-1-61779-086-7_16

Singh, A., Wang, H., Silva, L. C., Na, C., Prieto, M., Futerman, A. H., et al. (2012). Methylation of glycosylated sphingolipid modulates membrane lipid topography and pathogenicity of *Cryptococcus neoformans*. *Cell. Microbiol.* 14, 500-516. doi: 10.1111/j.1462-5822.2011.01735.x Teng, X., Dayhoff-Brannigan, M., Cheng, W. C., Gilbert, C. E., Sing, C. N., Diny, N. L., et al. (2013). Genome-wide consequences of deleting any single gene. *Mol. Cell.* 52, 485-494. doi: 10.1016/j.molcel.2013.09.026

Toffaletti, D. L., Rude, T. H., Johnston, S. A., Durack, D. T., and Perfect, J. R. (1993). Gene transfer in *Cryptococcus neoformans* by use of biolistic delivery of DNA. *J. Bacteriol.* 175, 1405-1411.

Tripathi, K., Mor, V., Bairwa, N. K., Del Poeta, M., and Mohanty, B. K. (2012). Hydroxyurea treatment inhibits proliferation of *Cryptococcus neoformans* in mice. *Front. Microbiol.* 3:187. doi: 10.3389/fmicb.2012.00187

Walraven, C. J., Gerstein, W., Hardison, S. E., Wormley, F., Lockhart, S. R., Harris, J. R., et al. (2011). Fatal disseminated *Cryptococcus gattii* infection in New Mexico. *PLoS ONE* 6:e28625. doi: 10.1371/journal.pone.0028625

Wang, Y., Aisen, P., and Casadevall, A. (1995). *Cryptococcus neoformans* melanin and virulence: mechanism of action. *Infect. Immun.* 63, 3131-3136.

Warnecke, D., Erdmann, R., Fahl, A., Hube, B., Muller, F., Zank, T., et al. (1999). Cloning and functional expression of UGT genes encoding sterol glucosyltransferases from *Saccharomyces cerevisiae, Candida albicans, Pichia pastoris*, and *Dictyostelium discoideum*. *J. Biol. Chem.* 274, 13048-13059. doi: 10.1074/jbc.274.19.13048

Watanabe, T., Ito, T., Goda, H. M., Ishibashi, Y., Miyamoto, T., Ikeda, K., et al. (2015). Sterylglucoside Catabolism in *Cryptococcus neoformans* with endoglycoceramidase-related protein 2 (EGCrP2), the first steryl-beta-glucosidase identified in fungi. *J. Biol. Chem.* 290, 1005-1019. doi: 10.1074/jbc.M114.616300

Wewer, V., Dombrink, I., Vom Dorp, K., and Dormann, P. (2011). Quantification of sterol lipids in plants by quadrupole time-of-flight mass spectrometry. *J. Lipid Res.* 52, 1039-1054. doi: 10.1194/jlr.D013987

Wormley, F. L. Jr., Perfect, J. R., Steele, C., and Cox, G. M. (2007). Protection against cryptococcosis by using a murine gamma interferon-producing *Cryptococcus neoformans* strain. *Infect. Immun.* 75, 1453-1462. doi: 10.1128/IAI.00274-06

Wozniak, K. L., Young, M. L., and Wormley, F. L. Jr. (2011). Protective immunity against experimental pulmonary cryptococcosis in T cell-depleted mice. *Clin. Vaccine Immunol.* 18, 717-723. doi: 10.1128/CVI.00036-11

Wright, L., Bubb, W., Davidson, J., Santangelo, R., Krockenberger, M., Himmelreich, U., et al. (2002). Metabolites released by *Cryptococcus neoformans* var. *neoformans* and var. *gattii* differentially affect human neutrophil function. *Microbes Infect.* 4, 1427-1438. doi: 10.1016/S 1286-4579(02)00024-2

Wunder, C., Churin, Y., Winau, F., Warnecke, D., Vieth, M., Lindner, B., et al. (2006). Cholesterol glucosylation promotes immune evasion by *Helicobacter pylori*. *Nat. Med.* 12, 1030-1038. doi: 10.1038/nm1480

What is claimed is:

1. A composition comprising a mutant fungus, wherein the endogenous Sterylglucosidase (Sgl1) gene is inactivated.

2. The composition of claim 1, wherein said mutant fungus lacks the ability to metabolize sterylglucosides (SGs).

3. The composition of claim 1, wherein said mutant fungus accumulates sterol glycosides.

4. The composition of claim 1, wherein said mutant fungus is avirulent.

5. The composition of claim 1, wherein said mutant fungus is from a *Cryptococcus* genus.

6. The composition of claim 1, wherein said mutant fungus is selected from the group consisting of *Cryptococcus neoformans, Cryptococcus gatii, Cryptococcus albidus, Cryptococcus uniguttulatus, Candida albicans, Aspergillus fumigatus* and other fungi in which the Sgl1 gene is deleted.

7. A method for producing sterylglucosides comprising:
providing a mutant fungus wherein the endogenous Sterylglucosidase (Sgl1) gene is inactivated;
growing the fungus, wherein the mutant fungus produces sterylglucosides; and
isolating said sterylglucosides.

8. The method of claim 7, wherein said mutant fungus lacks the ability to metabolize sterylglucosides (SGs).

9. The method of claim 7, wherein said mutant fungus accumulates sterol glycosides.

10. The method of claim 7, wherein said mutant fungus is from a *Cryptococcus* genus.

11. The method of claim 7, wherein said mutant fungus is selected from the group consisting of *Cryptococcus neoformans, Cryptococcus gatii, Cryptococcus albidus, Cryptococcus uniguttulatus, Candida albicans, Aspergillus fumigatus* and other fungi in which the Sgl1 gene is deleted.

* * * * *